(12) United States Patent
Yamauchi et al.

(10) Patent No.: US 11,208,410 B2
(45) Date of Patent: Dec. 28, 2021

(54) HETEROCYCLE-BOUND CONDENSED HETEROCYCLIC COMPOUND OR SALT THEREOF, AGRICULTURAL AND HORTICULTURAL INSECTICIDE COMPRISING THE COMPOUND, AND METHOD FOR USING THE INSECTICIDE

(71) Applicant: Nihon Nohyaku Co., Ltd., Tokyo (JP)

(72) Inventors: Chiaki Yamauchi, Osaka (JP); Ikki Yonemura, Osaka (JP); Akiyuki Suwa, Osaka (JP); Shunpei Fujie, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 485 days.

(21) Appl. No.: 16/077,971

(22) PCT Filed: Feb. 24, 2017

(86) PCT No.: PCT/JP2017/007162
§ 371 (c)(1),
(2) Date: Aug. 14, 2018

(87) PCT Pub. No.: WO2017/146221
PCT Pub. Date: Aug. 31, 2017

(65) Prior Publication Data
US 2020/0361940 A1 Nov. 19, 2020

(30) Foreign Application Priority Data
Feb. 26, 2016 (JP) ............................ JP2016-035076

(51) Int. Cl.
| C07D 487/04 | (2006.01) |
| C07D 213/80 | (2006.01) |
| C07D 237/20 | (2006.01) |
| C07D 401/12 | (2006.01) |
| C07D 471/04 | (2006.01) |
| A01N 43/40 | (2006.01) |
| A01N 43/58 | (2006.01) |
| A01N 43/90 | (2006.01) |

(52) U.S. Cl.
CPC ........... *C07D 487/04* (2013.01); *A01N 43/40* (2013.01); *A01N 43/58* (2013.01); *A01N 43/90* (2013.01); *C07D 213/80* (2013.01); *C07D 237/20* (2013.01); *C07D 401/12* (2013.01); *C07D 471/04* (2013.01)

(58) Field of Classification Search
None
See application file for complete search history.

(56) References Cited

U.S. PATENT DOCUMENTS

| 10,575,525 B2 | 3/2020 | Matsuo et al. |
| 2005/0124497 A1 | 6/2005 | Fusslein et al. |
| 2011/0039843 A1 | 2/2011 | Iwakoshi et al. |
| 2012/0015975 A1 | 1/2012 | Takahashi et al. |
| 2012/0108586 A1 | 5/2012 | Iwakoshi et al. |
| 2012/0178779 A1 | 7/2012 | Takahashi et al. |
| 2012/0196891 A1 | 8/2012 | Iwakoshi |
| 2012/0245167 A1 | 9/2012 | Iwakoshi et al. |
| 2013/0190271 A1 | 7/2013 | Iwakoshi et al. |
| 2013/0252981 A1 | 9/2013 | Takahashi et al. |
| 2013/0261141 A1 | 10/2013 | Bretschneider et al. |
| 2014/0018373 A1 | 1/2014 | Takyo et al. |
| 2014/0194290 A1 | 7/2014 | Takahashi et al. |

(Continued)

FOREIGN PATENT DOCUMENTS

| JP | 2008-308448 A | 12/2008 |
| JP | 2009-280574 A | 12/2009 |

(Continued)

OTHER PUBLICATIONS

Supplementary European Search Report for EP 17756655 dated Jun. 14, 2019.

(Continued)

*Primary Examiner* — Bethany P Barham
*Assistant Examiner* — Barbara S Frazier
(74) *Attorney, Agent, or Firm* — Knobbe, Martens, Olson & Bear, LLP

(57) ABSTRACT

In crop production in the fields of agriculture, horticulture and the like, the damage caused by insect pests etc. is still immense, and insect pests resistant to existing insecticides have emerged. To solve the problems, the present invention has been made, and an object of the present invention is to develop and provide a novel agricultural and horticultural insecticide.

The present invention provides a heterocycle-bound condensed heterocyclic compound represented by the general formula (1):

[Chem. 1]

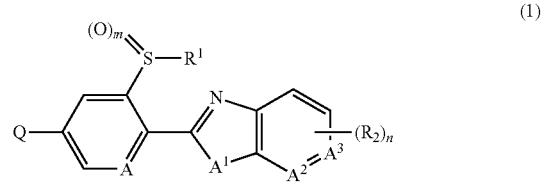

(1)

{wherein $R^1$ represents an ethyl group, $R^2$ represents a haloalkyl group, $A^1$ represents a N-methyl group, $A^2$ and $A^3$ represent a nitrogen atom, n represents 1, m represents 2, and Q represents an oxadiazole}, or a salt thereof; an agricultural and horticultural insecticide comprising the compound or a salt thereof as an active ingredient; and a method for using the insecticide.

7 Claims, No Drawings

(56) References Cited

U.S. PATENT DOCUMENTS

| | | |
|---|---|---|
| 2014/0364444 A1 | 12/2014 | Takyo et al. |
| 2015/0197532 A1 | 7/2015 | Takahashi et al. |
| 2015/0313234 A1 | 11/2015 | Takahashi et al. |
| 2016/0000081 A1 | 1/2016 | Shimizu et al. |
| 2016/0009715 A1 | 1/2016 | Takahashi et al. |
| 2016/0021886 A1 | 1/2016 | Yonemura et al. |
| 2016/0159743 A1 | 6/2016 | Takahashi et al. |
| 2017/0073342 A1 | 3/2017 | Fischer et al. |
| 2017/0240554 A1 | 8/2017 | Edmunds et al. |
| 2017/0267672 A1 | 9/2017 | Stoller et al. |

FOREIGN PATENT DOCUMENTS

| | | |
|---|---|---|
| JP | 2010-275301 A | 12/2010 |
| JP | 2011-79774 A | 4/2011 |
| JP | 2012-131780 A | 7/2012 |
| WO | WO 2006/128867 A1 | 12/2006 |
| WO | WO 2012/086848 A1 | 6/2012 |
| WO | WO 2013/018928 A1 | 2/2013 |
| WO | WO 2014/104407 A1 | 7/2014 |
| WO | WO 2014/125651 A1 | 8/2014 |
| WO | WO 2015/121136 A1 | 8/2015 |
| WO | WO 2015/198859 A1 | 12/2015 |
| WO | WO 2016/023954 A2 | 2/2016 |
| WO | WO 2016/030229 A1 | 3/2016 |
| WO | WO 2016/059145 A1 | 4/2016 |

OTHER PUBLICATIONS

International Search Report for PCT/JP2017/007162 dated Apr. 18, 2017.
International Preliminary Report on Patentability for PCT/JP2017/007162 dated Aug. 28, 2018.
Office Action for Egyptian Patent Application No. PCT1228/2018, dated Jun. 17, 2021.

HETEROCYCLE-BOUND CONDENSED HETEROCYCLIC COMPOUND OR SALT THEREOF, AGRICULTURAL AND HORTICULTURAL INSECTICIDE COMPRISING THE COMPOUND, AND METHOD FOR USING THE INSECTICIDE

CROSS REFERENCE TO RELATED APPLICATIONS

This application is a U.S. National Phase Application of PCT International Application No. PCT/JP2017/007162, filed on Feb. 24, 2017, designating the United States of America and published in the Japanese language, which is an International Application of and claims the benefit of priority to Japanese Patent Application No. 2016-035076, filed on Feb. 26, 2016. The disclosures of the above-referenced applications are hereby expressly incorporated by reference in their entireties.

TECHNICAL FIELD

The present invention relates to an agricultural and horticultural insecticide comprising a heterocycle-bound condensed heterocyclic compound or a salt thereof as an active ingredient, and a method for using the insecticide.

BACKGROUND ART

Various compounds have been examined for their potential as agricultural and horticultural insecticides, and among them, certain kinds of condensed heterocyclic compounds have been reported to be useful as insecticides (for example, see Patent Literature 1 to 7). The literature, however, does not disclose any heterocycle-bound condensed heterocyclic compound.

CITATION LIST

Patent Literature

Patent Literature 1: JP-A 2009-280574
Patent Literature 2: JP-A 2010-275301
Patent Literature 3: JP-A 2011-79774
Patent Literature 4: JP-A 2012-131780
Patent Literature 5: WO 2012/086848
Patent Literature 6: WO 2013/018928
Patent Literature 7: WO 2015/121136

SUMMARY OF INVENTION

Technical Problem

In crop production in the fields of agriculture, horticulture and the like, the damage caused by insect pests etc. is still immense, and insect pests resistant to existing insecticides have emerged. Under such circumstances, the development of novel agricultural and horticultural insecticides is desired.

Solution to Problem

The present inventors conducted extensive research to solve the above-described problems. As a result, the present inventors found that a heterocycle-bound condensed heterocyclic compound represented by the general formula (1) or a salt thereof is highly effective for the control of agricultural and horticultural pests, and reached the completion of the present invention.

That is, the present invention includes the following.

[1] A heterocycle-bound condensed heterocyclic compound represented by the general formula (1):

[Chem. 1]

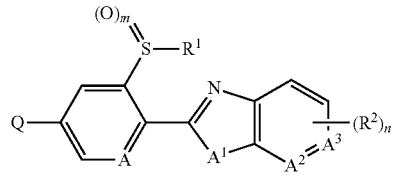

(1)

{wherein
$R^1$ represents (a1) a ($C_1$-$C_6$) alkyl group,
$R^2$ represents
(b1) a halogen atom;
(b2) a cyano group;
(b3) a nitro group;
(b4) a halo ($C_1$-$C_6$) alkyl group;
(b5) a halo ($C_1$-$C_6$) alkoxy group;
(b6) a halo ($C_1$-$C_6$) alkylthio group;
(b7) a halo ($C_1$-$C_6$) alkylsulfinyl group; or
(b8) a halo ($C_1$-$C_6$) alkylsulfonyl group,
Q represents any one of the groups represented by the following Q-1 to Q-4:

[Chem. 2]

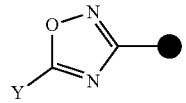
Q-1

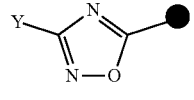
Q-2

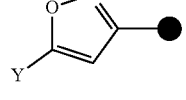
Q-3

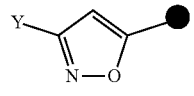
Q-4

(wherein
Y represents
(c1) a hydrogen atom;
(c2) a halogen atom;
(c3) a cyano group;
(c4) a hydroxyl group;
(c5) a ($C_1$-$C_6$) alkyl group;
(c6) a ($C_3$-$C_6$) cycloalkyl group;
(c7) a ($C_1$-$C_6$) alkoxy group;
(c8) a ($C_2$-$C_6$) alkenyloxy group;
(c9) a ($C_2$-$C_6$) alkynyloxy group;
(c10) a halo ($C_1$-$C_6$) alkyl group;
(c11) a halo ($C_1$-$C_6$) alkoxy group;

(c12) a cyano ($C_1$-$C_6$) alkoxy group;
(c13) $NR^4R^5$ (wherein $R^4$ and $R^5$ may be the same or different and each represent (a) a hydrogen atom; (b) a ($C_1$-$C_6$) alkyl group; (c) a ($C_1$-$C_6$) alkylcarbonyl group; or (d) a ($C_1$-$C_6$) alkoxycarbonyl group);
(c14) a ($C_1$-$C_6$) alkoxycarbonyl group;
(c15) a $NR^4R^5$ carbonyl group (wherein $R^4$ and $R^5$ are as defined above); or
(c16) a phenyl group, and
each black solid circle represents a binding position),
A, $A^2$ and $A^3$ may be the same or different and each represent CH or a nitrogen atom,
$A^1$ represents an oxygen atom; a sulfur atom; or N—$R^3$ (wherein $R^3$ represents (d1) a ($C_1$-$C_6$) alkyl group),
m represents 0; 1; or 2, and
n represents 1 or 2}
or a salt thereof.
[2] The heterocycle-bound condensed heterocyclic compound or the salt according to the above [1], wherein
$R^1$ is (a1) a ($C_1$-$C_6$) alkyl group,
$R^2$ is
(b4) a halo ($C_1$-$C_6$) alkyl group or
(b5) a halo ($C_1$-$C_6$) alkoxy group,
Q is Q-1 or Q-2,
Y is
(c1) a hydrogen atom;
(c5) a ($C_1$-$C_6$) alkyl group;
(c6) a ($C_3$-$C_6$) cycloalkyl group;
(c10) a halo ($C_1$-$C_6$) alkyl group;
(c11) a halo ($C_1$-$C_6$) alkoxy group; or
(c16) a phenyl group,
A, $A^2$ and $A^3$ are nitrogen atoms,
$A^1$ is N—$R^3$ (wherein $R^3$ is as defined above),
m is 2, and
n is 1.
[3] An agricultural and horticultural insecticide comprising the heterocycle-bound condensed heterocyclic compound or the salt according to the above [1] or [2] as an active ingredient.
[4] A method for using the agricultural and horticultural insecticide according to the above [3], the method comprising applying an effective amount of the heterocycle-bound condensed heterocyclic compound or the salt according to the above [1] or [2] to plants or soil.
[5] An animal ectoparasite control agent comprising the heterocycle-bound condensed heterocyclic compound or the salt according to the above [1] or [2] as an active ingredient.
[6] A condensed heterocyclic compound represented by the general formula (1):

[Chem. 3]

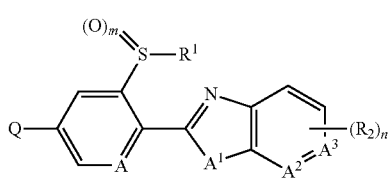

(1)

{wherein
$R^1$ represents (a1) a ($C_1$-$C_6$) alkyl group,
$R^2$ represents
(b1) a halogen atom;
(b2) a cyano group;
(b3) a nitro group;
(b4) a halo ($C_1$-$C_6$) alkyl group;
(b5) a halo ($C_1$-$C_6$) alkoxy group;
(b6) a halo ($C_1$-$C_6$) alkylthio group;
(b7) a halo ($C_1$-$C_6$) alkylsulfinyl group; or
(b8) a halo ($C_1$-$C_6$) alkylsulfonyl group,
Q represents any one of the following:

[Chem. 4]

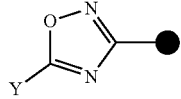 Q-1

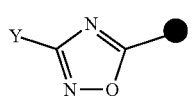 Q-2

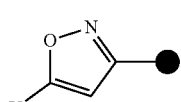 Q-3

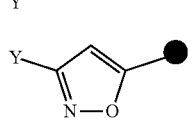 Q-4

(wherein
Y represents
(c1) a hydrogen atom;
(c2) a halogen atom;
(c3) a cyano group;
(c4) a hydroxyl group;
(c5) a ($C_1$-$C_6$) alkyl group;
(c6) a ($C_3$-$C_6$) cycloalkyl group;
(c7) a ($C_1$-$C_6$) alkoxy group;
(c8) a ($C_2$-$C_6$) alkenyloxy group;
(c9) a ($C_2$-$C_6$) alkynyloxy group;
(c10) a halo ($C_1$-$C_6$) alkyl group;
(c11) a halo ($C_1$-$C_6$) alkoxy group;
(c12) a cyano ($C_1$-$C_6$) alkoxy group;
(c13) $NR^4R^5$ (wherein $R^4$ and $R^5$ may be the same or different and each represent (a) a hydrogen atom; (b) a ($C_1$-$C_6$) alkyl group; (c) a ($C_1$-$C_6$) alkylcarbonyl group; or (d) a ($C_1$-$C_6$) alkoxycarbonyl group);
(c14) a ($C_1$-$C_6$) alkoxycarbonyl group;
(c15) a $NR^4R^5$ carbonyl group (wherein $R^4$ and $R^5$ are as defined above); or
(c16) a phenyl group, and
each black solid circle represents a binding position),
A, $A^2$ and $A^3$ each represent CH or a nitrogen atom,
$A^1$ represents O, S or N—$R^3$ (wherein $R^3$ represents (d1) a ($C_1$-$C_6$) alkyl group),
m represents 0, 1 or 2, and
n represents 1 or 2}.
[7] The condensed heterocyclic compound according to the above [6], wherein
$R^1$ represents (a1) a ($C_1$-$C_6$) alkyl group,
$R^2$ represents
(b4) a halo ($C_1$-$C_6$) alkyl group or
(b5) a halo ($C_1$-$C_6$) alkoxy group,
Q represents Q-1 or Q-2,
Y represents
(c1) a hydrogen atom;
(c5) a ($C_1$-$C_6$) alkyl group;

(c6) a $(C_3-C_6)$ cycloalkyl group;
(c10) a halo $(C_1-C_6)$ alkyl group;
(c11) a halo $(C_1-C_6)$ alkoxy group; or
(c16) a phenyl group, and
    A, $A^2$ and $A^3$ represent a nitrogen atom,
    $A^1$ represents N—$R^3$,
    m represents 2, and
    n represents 1.

[8] An agricultural and horticultural insecticide comprising the condensed heterocyclic compound according to the above [6] or [7] as an active ingredient.

[9] A method for using an agricultural and horticultural insecticide, the method comprising applying an effective amount of the condensed heterocyclic compound according to the above [6] or [7] to plants or soil.

[10] An animal ectoparasite control agent comprising an effective amount of the condensed heterocyclic compound according to the above [6] or [7] as an active ingredient.

Advantageous Effects of Invention

The heterocycle-bound condensed heterocyclic compound of the present invention or a salt thereof is not only highly effective as an agricultural and horticultural insecticide but also effective against pests which live on non-human animals including pets such as dogs and cats and domestic animals such as cattle and sheep.

DESCRIPTION OF EMBODIMENTS

In the definition of the heterocycle-bound condensed heterocyclic compound represented by the general formula (1) of the present invention or a salt thereof, "halo" refers to a "halogen atom" and represents a chlorine atom, a bromine atom, an iodine atom or a fluorine atom.

The "$(C_1-C_6)$ alkyl group" refers to a straight-chain or branched-chain alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, a 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethyl propyl group, a 3,3-dimethylbutyl group or the like.

The "$(C_3-C_6)$ cycloalkyl group" refers to a cyclic alkyl group of 3 to 6 carbon atoms, for example, a cyclopropyl group, a cyclobutyl group, a cyclopentyl group, a cyclohexyl group or the like. The "$(C_1-C_6)$ alkoxy group" refers to a straight-chain or branched-chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, a 1-ethylpropyloxy group, a 1-methylbutyloxy group, a n-hexyloxy group, an isohexyloxy group, a 1,1,2-trimethylpropyloxy group or the like. The "$(C_2-C_6)$ alkenyloxy group" refers to a straight-chain or branched-chain alkenyloxy group of 2 to 6 carbon atoms, for example, a propenyloxy group, a butenyloxy group, a pentenyloxy group, a hexenyloxy group or the like. The "$(C_2-C_6)$ alkynyloxy group" refers to a straight-chain or branched-chain alkynyloxy group of 2 to 6 carbon atoms, for example, a propynyloxy group, a butynyloxy group, a pentynyloxy group, a hexynyloxy group or the like.

The "$(C_1-C_6)$ alkylthio group" refers to a straight-chain or branched-chain alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a tert-pentylthio group, a neopentylthio group, a 2,3-dimethylpropylthio group, a 1-ethylpropylthio group, a 1-methylbutylthio group, a n-hexylthio group, an isohexylthio group, a 1,1,2-trimethylpropylthio group or the like. The "$(C_1-C_6)$ alkylsulfinyl group" refers to a straight-chain or branched-chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a tert-pentylsulfinyl group, a neopentylsulfinyl group, a 2,3-dimethylpropylsulfinyl group, a 1-ethylpropylsulfinyl group, a 1-methylbutylsulfinyl group, a n-hexylsulfinyl group, an isohexylsulfinyl group, a 1,1,2-trimethylpropylsulfinyl group or the like. The "$(C_1-C_6)$ alkylsulfonyl group" refers to a straight-chain or branched-chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, a 1-ethylpropylsulfonyl group, a 1-methylbutylsulfonyl group, a n-hexylsulfonyl group, an isohexylsulfonyl group, a 1,1,2-trimethylpropylsulfonyl group or the like.

The "$(C_1-C_6)$ alkylcarbonyl group" refers to an alkylcarbonyl group having a $(C_1-C_6)$ alkyl group, that is, an alkylcarbonyl group of 2 to 7 carbon atoms, for example, an acetyl group, a propanoyl group, a butanoyl group, a 2-methylpropanoyl group, a pentanoyl group, a 2-methylbutanoyl group, a 3-methylbutanoyl group, a pivaloyl group, a hexanoyl group, a cyclopropylcarbonyl group or the like.

The "$(C_1-C_6)$ alkoxycarbonyl group" refers to an alkoxycarbonyl group having a $(C_1-C_6)$ alkoxy group, that is, an alkoxycarbonyl group of 2 to 7 carbon atoms, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a pentyloxycarbonyl group or the like.

The above-mentioned "$(C_1-C_6)$ alkyl group",
"$(C_3-C_6)$ cycloalkyl group",
"$(C_1-C_6)$ alkoxy group",
"$(C_2-C_6)$ alkenyloxy group",
"$(C_2-C_6)$ alkynyloxy group",
"$(C_1-C_6)$ alkylthio group",
"$(C_1-C_6)$ alkylsulfinyl group" and
"$(C_1-C_6)$ alkylsulfonyl group"
may be substituted with one or more halogen atoms at a substitutable position(s), and in the case where any of the above-listed groups is substituted with two or more halogen atoms, the halogen atoms may be the same or different.

The above-mentioned "groups substituted with one or more halogen atoms" are expressed as
a "halo $(C_1-C_6)$ alkyl group",
a "halo $(C_3-C_6)$ cycloalkyl group",
a "halo $(C_1-C_6)$ alkoxy group",
a "halo $(C_2-C_6)$ alkenyloxy group",
a "halo $(C_2-C_6)$ alkynyloxy group",
a "halo $(C_1-C_6)$ alkylthio group", a "halo ($C_1$-$C_6$) alkylsulfinyl group" and
a "halo ($C_1$-$C_6$) alkylsulfonyl group".

The expressions "($C_1$-$C_6$)", "($C_2$-$C_6$)", "($C_3$-$C_6$)", etc. each refer to the range of the number of carbon atoms in each group. The same definition holds true for groups in which two or more of the above-mentioned groups are coupled together, and for example, the "($C_1$-$C_6$) alkoxy ($C_1$-$C_6$) alkyl group" means that a straight-chain or branched-chain alkoxy group of 1 to 6 carbon atoms is bound to a straight-chain or branched-chain alkyl group of 1 to 6 carbon atoms.

Examples of the salt of the heterocycle-bound condensed heterocyclic compound represented by the general formula (1) of the present invention include inorganic acid salts, such as hydrochlorides, sulfates, nitrates and phosphates; organic acid salts, such as acetates, fumarates, maleates, oxalates, methanesulfonates, benzenesulfonates and p-toluene-sulfonates; and salts with an inorganic or organic base such as a sodium ion, a potassium ion, a calcium ion and a trimethylammonium ion.

The heterocycle-bound condensed heterocyclic compound represented by the general formula (1) of the present invention and a salt thereof can have one or more chiral centers in the structural formula, and can exist as two or more kinds of optical isomers or diastereomers. All the optical isomers and mixtures of the isomers at any ratio are also included in the present invention. Further, the heterocycle-bound condensed heterocyclic compound represented by the general formula (1) of the present invention and a salt thereof can exist as two kinds of geometric isomers due to a carbon-carbon double bond in the structural formula. All the geometric isomers and mixtures of the isomers at any ratio are also included in the present invention.

In preferable embodiments for use as an insecticide, the heterocycle-bound condensed heterocyclic compound represented by the general formula (1) or a salt thereof is the one in which $R^1$ is (a1) a ($C_1$-$C_6$) alkyl group,
$R^2$ is
(b4) a halo ($C_1$-$C_6$) alkyl group or
(b5) a halo ($C_1$-$C_6$) alkoxy group,
   Q is Q-1 or Q-2,
   Y is
(c1) a hydrogen atom;
(c5) a ($C_1$-$C_6$) alkyl group;
(c6) a ($C_3$-$C_6$) cycloalkyl group;
(c10) a halo ($C_1$-$C_6$) alkyl group;
(c11) a halo ($C_1$-$C_6$) alkoxy group; or
(c16) a phenyl group,
   A, $A^2$ and $A^3$ are nitrogen atoms,
   $A^1$ is N—$R^3$ (wherein $R^3$ is (d1) a ($C_1$-$C_6$) alkyl group),
   m is 2, and
   n is 1.

The heterocycle-bound condensed heterocyclic compound of the present invention or a salt thereof can be produced according to, for example, the production methods described below, which are non-limiting examples.

Production Method 1

[Chem. 5]

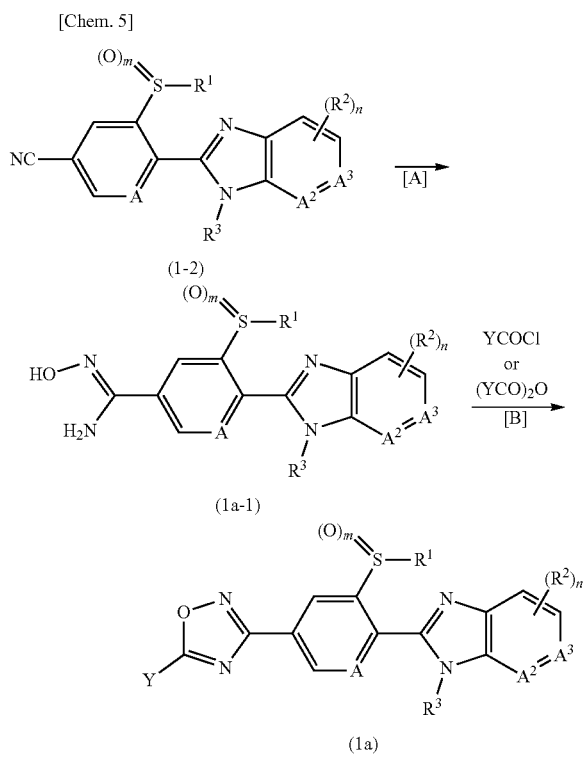

In the formula, $R^1$, $R^2$, $R^3$, A, $A^2$, $A^3$, Y, m and n are as defined above.

The heterocycle-bound condensed heterocyclic compound represented by the general formula (1a) of the present invention can be produced through the steps [A] and [B] described below.

Step [A]

A step of converting the cyano group of the compound represented by the general formula (1-2) to an amidoxime group, for producing the compound represented by the general formula (1a-1).

Step [B]

A step of cyclizing the heterocycle-bound condensed heterocyclic compound represented by the general formula (1a-1) by the reaction of the amidoxime group with a carboxylic anhydride or a carboxylic chloride, for producing the compound represented by the general formula (1a).

Production Method at Step [A]

The compound represented by the general formula (1a-1) can be produced by reacting the compound represented by the general formula (1-2) with a hydroxylamine salt in the presence of a base and an inert solvent.

Examples of the hydroxylamine salt used in this reaction include a hydroxylamine hydrochloride and a hydroxylamine sulfate.

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (1-2).

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether (MTBE), dioxane and tetrahydrofuran; esters such as ethyl acetate; amides such as dimethylformamide and dimethylacetamide; ketones such as acetone and methyl ethyl ketone; and polar solvents such as dimethyl sulfoxide, 1,3-dimethyl-2-imidazolidinone and water. One of these inert solvents may be used alone, and also two or more of them may be used as a mixture. The amount of the inert solvent used is usually selected as appropriate from the range of 0.1 to 100 L relative to 1 mol of the compound represented by the general formula (1-2).

Since this reaction is an equimolar reaction of the reactants, they are basically used in equimolar amounts, but either of them may be used in an excess amount. The reaction temperature is usually in the range of room temperature to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [B]

The heterocycle-bound condensed heterocyclic compound represented by the general formula (1a) can be produced by reacting the compound represented by the general formula (1a-1) with an appropriate carboxylic anhydride ((YCO)$_2$O) or carboxylic chloride (YCOCl) in the presence of a base and an inert solvent.

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (1a-1).

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (1a-1).

The reaction temperature is usually in the range of room temperature to the boiling point of the inert solvent used. The reaction time varies with the reaction scale and the reaction temperature, but is usually in the range of a few minutes to 48 hours.

After the reaction is completed, the compound of interest is isolated from the post-reaction mixture by the usual method. As needed, recrystallization, column chromatography, etc. can be employed for the purification of the compound of interest.

Production Method 2

[Chem.6]

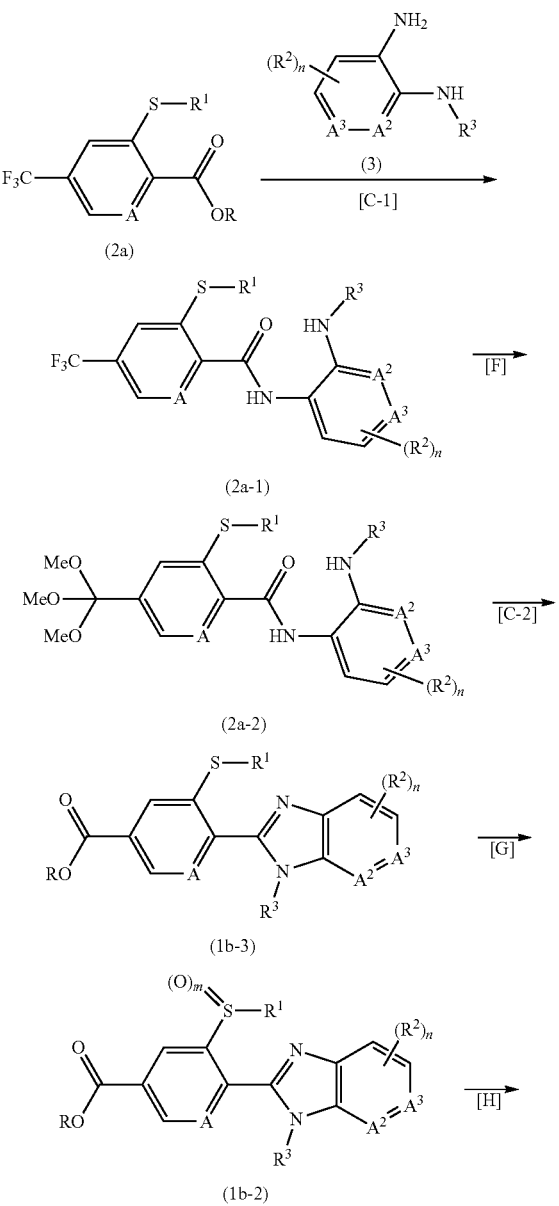

-continued

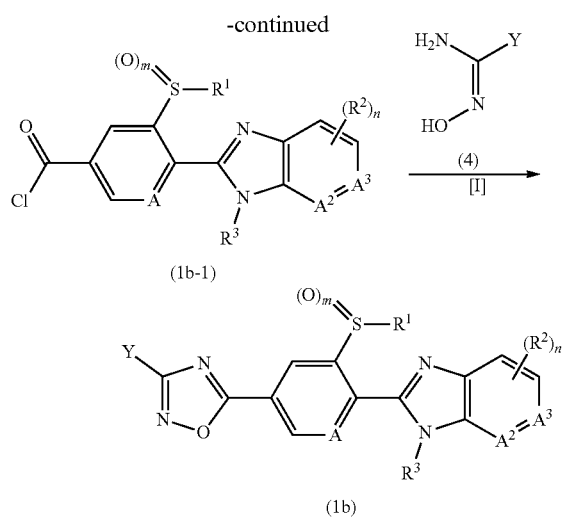

(1b-1)

(1b)

In the formula, R, $R^1$, $R^2$, $R^3$, A, $A^2$, $A^3$, Y, m and n are as defined above.

The heterocycle-bound condensed heterocyclic compound represented by the general formula (1b) of the present invention can be produced through the steps [C-1] to [I] described below.

Step [C-1]

A step of reacting the compound represented by the general formula (2a) with the compound represented by the general formula (3), for producing the compound represented by the general formula (2a-1).

Step [F]

A step of converting the trifluoromethyl group of the compound represented by the general formula (2a-1) to a trimethoxy methyl group, for producing the compound represented by the general formula (2a-2).

Step [C-2]

A step of intramolecularly cyclizing the compound represented by the general formula (2a-2) under acidic conditions and converting the trimethoxy methyl group to an ester group, for producing the compound represented by the general formula (1b-3).

Step [G]

A step of oxidizing the compound represented by the general formula (1b-3), for producing the compound represented by the general formula (1b-2).

Step [H]

A step of converting the ester group of the compound represented by the general formula (1b-2) to an acid chloride group, for producing the compound represented by the general formula (1b-1).

Step [I]

A step of reacting the compound represented by the general formula (1b-1) with the compound represented by the general formula (4) and further reacting the resulting compound with YCOCl or $(YCO)_2O$ in the same manner as described in Step [B] of the above Production Method 1, for producing the heterocycle-bound condensed heterocyclic compound represented by the general formula (1b).

Production Method at Step [C-1]

The compound represented by the general formula (2a-1) can be produced by reacting the compound represented by the general formula (2a) produced by a known method with the compound represented by the general formula (3) in the presence of a base and an inert solvent.

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (2a).

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (2a).

Since this reaction is an equimolar reaction of the reactants, they are basically used in equimolar amounts, but either of them may be used in an excess amount. The reaction temperature is usually in the range of room temperature to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [F]

The compound represented by the general formula (2a-2) can be produced by reacting the compound of the general formula (2a-1) produced at the previous step with sodium methoxide.

The inert solvent used in this reaction may be any solvent that does not markedly inhibit the reaction, and the examples include aromatic hydrocarbons such as benzene, toluene and xylene; halogenated hydrocarbons such as chlorobenzene and dichlorobenzene; and aromatic heterocycles such as pyridine. One of these inert solvents may be used alone, and also two or more of them may be used as a mixture. The amount of the inert solvent used is usually selected as appropriate from the range of 0.1 to 100 L relative to 1 mol of the compound represented by the general formula (2a-1). In the case where sodium methoxide in methanol is used, it is not necessary to use an inert solvent.

The reaction temperature is usually in the range of about 0° C. to the boiling point of the solvent used. The reaction time varies with the reaction scale, the reaction temperature and the like, but is usually selected as appropriate from the range of a few minutes to 48 hours. The amount of the sodium methoxide used in this reaction is usually in the range of an about 3- to 10-fold molar amount relative to the compound represented by the general formula (2a-1). After the reaction is completed, the compound of interest is isolated from the post-reaction mixture by the usual method. As needed, recrystallization, column chromatography, etc. can be employed for the purification of the compound of interest.

Production Method at Step [C-2]

The compound represented by the general formula (1b-3) can be produced by allowing the compound represented by the general formula (2a-2) to react under acidic conditions.

Examples of the acid used in this reaction include inorganic acids such as hydrochloric acid, sulfuric acid and nitric acid; organic acids such as formic acid, acetic acid, propionic acid, trifluoroacetic acid and benzoic acid; sulfonic acids such as methanesulfonic acid and trifluoromethanesulfonic acid; and phosphoric acid. The amount of the acid used is usually selected as appropriate from the range of a 0.01- to 10-fold molar amount relative to the compound represented by the general formula (2a-2).

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (2a-2).

After the reaction is completed, the compound of interest is isolated from the post-reaction mixture by the usual method. As needed, recrystallization, column chromatography, etc. can be employed for the purification of the compound of interest.

Production Method at Step [G]

The compound represented by the general formula (1b-2) can be produced by reacting the compound represented by the general formula (1b-3) with an oxidizing agent in an inert solvent.

Examples of the oxidizing agent used in this reaction include peroxides such as a hydrogen peroxide solution, perbenzoic acid and m-chloroperoxybenzoic acid. The amount of the oxidizing agent used is usually selected as appropriate from the range of a 1- to 10-fold molar amount relative to the compound represented by the general formula (1b-3).

The inert solvent used in this reaction may be any solvent that does not markedly inhibit the reaction, and the examples include straight-chain or cyclic ethers such as diethyl ether, tetrahydrofuran and dioxane; aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; organic acids such as formic acid and acetic acid; and polar solvents such as N,N-dimethylformamide, N,N-dimethylacetamide, 1,3-dimethyl-2-imidazolidinone and water. One of these inert solvents may be used alone, and also two or more of them may be used as a mixture. The amount of the inert solvent used is usually selected as appropriate from the range of 0.1 to 100 L relative to 1 mol of the compound represented by the general formula (1b-3).

The reaction temperature is usually selected as appropriate from the range of −10° C. to the reflux temperature of the inert solvent used. The reaction time varies with the reaction scale, the reaction temperature and the like and is not the same in every case, but is usually selected as appropriate from the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [H]

The compound represented by the general formula (1b-1) can be produced by hydrolyzing the compound represented by the general formula (1b-2) in the usual manner of organic synthesis and reacting the resulting compound with a chlorinating agent.

Production Method at Step [I]

The compound represented by the general formula (1b) can be produced by reacting the compound represented by the general formula (1b-1) with the compound represented by the general formula (4) and subjecting the resulting compound to the reaction as described in Step [B] of the above Production Method 1.

Production Method of Intermediate Represented by General Formula (1-2)

[Chem. 7]

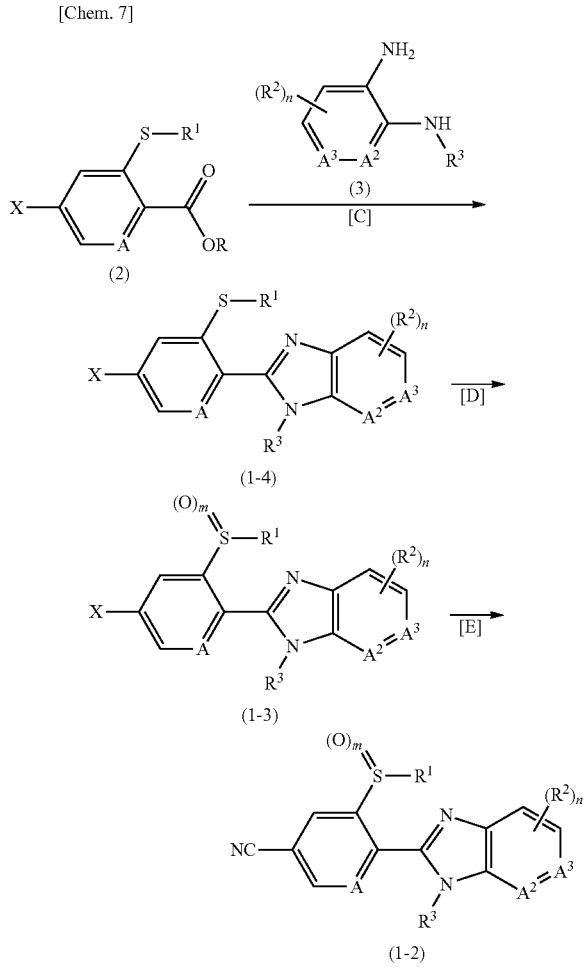

In the formula, $R^1$, $R^2$, $R^3$, A, $A^2$, $A^3$, m and n are as defined above, X represents a halogen atom, and R represents a ($C_1$-$C_3$) alkyl group. The "($C_1$-$C_3$) alkyl group" refers to a methyl group, an ethyl group, a n-propyl group or an isopropyl group.

The intermediate represented by the general formula (1-2) can be produced through the steps [C] to [E] described below.

Step [C]

A step of reacting the compound represented by the general formula (2) with the compound represented by the general formula (3), for producing the compound represented by the general formula (1-4).

Step [D]

A step of oxidizing the compound represented by the general formula (1-4), for producing the compound represented by the general formula (1-3).

Step [E]

A step of converting the halogen atom of the compound represented by the general formula (1-3) to a cyano group, for producing the intermediate represented by the general formula (1-2).

Production Method at Step [C]

The compound represented by the general formula (1-4) can be produced by synthesizing an amide compound from the compound represented by the general formula (2) and the compound represented by the general formula (3) in the same manner as described in Step [C-1] of the above Production Method 2, and subsequently subjecting the amide compound to the reaction as described in Step [C-2] of the above Production Method 2.

Production Method at Step [D]

The compound represented by the general formula (1-3) can be produced from the compound represented by the general formula (1-4) in the same manner as described in Step [G] of the above Production Method 2.

Production Method at Step [E]

The intermediate represented by the general formula (1-2) can be produced by what is called the Rosenmund-von Braun reaction (Ber. Dtsch. Chem. Ges. 1919, 52, 1749) of the compound represented by the general formula (1-3) with a cyanide in the presence of an inert solvent.

Examples of the cyanide that can be used in this reaction include sodium cyanide, potassium cyanide, zinc cyanide and copper cyanide.

The inert solvent used in this reaction may be any solvent that does not markedly inhibit the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; and aromatic heterocycles such as pyridine. One of these inert solvents may be used alone, and also two or more of them may be used as a mixture. The amount of the inert solvent used is usually selected as appropriate from the range of 0.1 to 100 L relative to 1 mol of the compound represented by the general formula (1-3).

The reaction temperature is usually in the range of about 0° C. to the boiling point of the solvent used. The reaction time varies with the reaction scale, the reaction temperature and the like, but is usually selected as appropriate from the range of a few minutes to 48 hours. The amount of the cyanide used in this reaction is usually in the range of an about 1- to 5-fold molar amount relative to the compound represented by the general formula (1-3). After the reaction is completed, the compound of interest is isolated from the post-reaction mixture by the usual method. As needed, recrystallization, column chromatography, etc. can be employed for the purification of the compound of interest.

Production Method of Intermediate Represented by General Formula (2)

[Chem. 8]

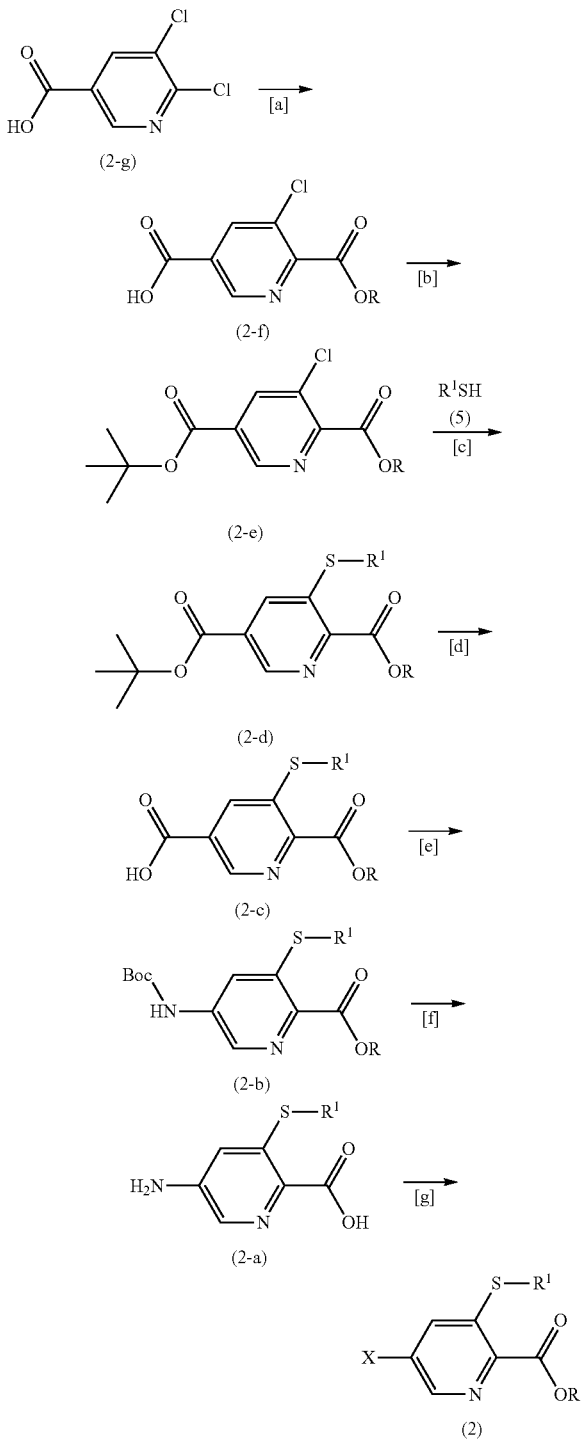

In the formula, R, $R^1$ and X are as defined above, and Boc represents a tert-butoxycarbonyl group.

The intermediate represented by the general formula (2) can be produced through the steps [a] to [g] described below.

Step [a]
A step of replacing the halogen atom at the C-2 position of the compound represented by the general formula (2-g) with an ester group, for producing the compound represented by the general formula (2-f).

Step [b]
A step of introducing a protective group by esterification of the compound represented by the general formula (2-f), for producing the compound represented by the general formula (2-e).

Step [c]
A step of reacting the compound represented by the general formula (2-e) with the compound represented by the general formula (5), for producing the compound represented by the general formula (2-d).

Step [d]
A step of deprotecting the compound represented by the general formula (2-d) under acidic conditions, for producing the compound represented by the general formula (2-c).

Step [e]
A step of converting the carboxyl group of the compound represented by the general formula (2-c) to a tert-butoxycarbonylamino group through the Curtius rearrangement, for producing the compound represented by the general formula (2-b).

Step [f]
A step of deprotecting the compound represented by the general formula (2-b) under acidic conditions, for producing the compound represented by the general formula (2-a).

Step [g]
A step of subjecting the compound represented by the general formula (2-a) to the Sandmeyer reaction and esterification, for producing the intermediate represented by the general formula (2).

Production Method at Step [a]
The compound represented by the general formula (2-f) can be produced from a commercial product of the compound represented by the general formula (2-g) in the same manner as described in JP-A 2005-272338.

Production Method at Step [b]
In the first substep of the production of the compound represented by the general formula (2-e), a carboxylic chloride can be produced by chlorinating the compound represented by the general formula (2-f) in the presence of a chlorinating agent and an inert solvent.

Examples of the inert solvent used in this reaction include ethers such as tetrahydrofuran (THF), ethylene glycol dimethyl ether, methyl tert-butyl ether and 1,4-dioxane; aromatic hydrocarbons such as toluene and xylene; halogenated hydrocarbons such as dichloromethane and chloroform; and a mixture thereof. The amount of the inert solvent used is usually selected as appropriate from the range of 0.1 to 100 L relative to 1 mol of the compound represented by the general formula (2-f).

Examples of the chlorinating agent used in this reaction include thionyl chloride, oxalyl chloride and phosphorus oxychloride. The amount of the chlorinating agent used is usually in the range of a 1- to 10-fold molar amount relative to the compound represented by the general formula (2-f). The reaction temperature is usually in the range of 0 to 100° C. The reaction time varies with the reaction scale and the reaction temperature, but is usually in the range of 0.1 to 24 hours. After the completion of the reaction, the solvent, the excess chlorinating agent, etc. are evaporated off to give a carboxylic chloride.

In the second production substep, the compound represented by the general formula (2-e) can be produced by reacting the carboxylic chloride with a tert-butyl alcohol in the presence of a base and an inert solvent.

Examples of the solvent used in this reaction include ethers such as THF, ethylene glycol dimethyl ether, tert-butyl methyl ether and 1,4-dioxane; aromatic hydrocarbons such as toluene and xylene; halogenated hydrocarbons such as dichloromethane and chloroform; and a mixture thereof. The amount of the solvent used is usually selected as appropriate from the range of 0.1 to 100 L relative to 1 mol of the compound represented by the general formula (2-f).

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the carboxylic chloride.

Production Method at Step [c]
The compound represented by the general formula (2-d) can be produced by reacting the compound represented by the general formula (2-e) with the compound represented by the general formula (5) in the presence of a base and an inert solvent.

Examples of the base used in this reaction include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (2-e).

In the case where an alkali metal salt of the compound represented by the general formula (5) is used, it is not necessary to use a base.

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (2-e).

Since this reaction is an equimolar reaction of the reactants, the compound represented by the general formula (5) and the compound represented by the general formula (2-e) are used basically in equimolar amounts, but either of them may be used in an excess amount. The reaction temperature is usually in the range of −10° C. to the boiling point of the inert solvent used. The reaction time varies with the reaction scale and the reaction temperature, but is usually in the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [d]

The compound represented by the general formula (2-c) can be produced by allowing the compound represented by the general formula (2-d) to react in the presence of an acid and/or an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; and sulfonic acids such as methanesulfonic acid and trifluoromethanesulfonic acid. The amount of the acid used is usually selected as appropriate from the range of a 1- to 10-fold molar amount relative to the compound represented by the general formula (2-d). In some cases, the acid can be used to serve as the solvent as well.

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (2-d). In the case where the acid is used as the solvent, it is not necessary to use another solvent.

The reaction temperature is usually in the range of room temperature to the boiling point of the inert solvent used. The reaction time varies with the reaction scale and the reaction temperature, but is usually in the range of a few minutes to 48 hours.

After the reaction is completed, the compound of interest is isolated from the post-reaction mixture by the usual method. As needed, recrystallization, column chromatography, etc. can be employed for the purification of the compound of interest.

Production Method at Step [e]

The compound represented by the general formula (2-b) can be produced by reacting the compound represented by the general formula (2-c) with DPPA (diphenylphosphoryl azide) in the presence of a tert-butyl alcohol according to the method described in J. A. Chem. Soc. 1972, 94, 6203-6205.

Production Method at Step [f]

The compound represented by the general formula (2-a) can be produced by allowing the compound represented by the general formula (2-b) to react in the presence of an acid and an inert solvent.

Examples of the acid used in this reaction include inorganic acids such as hydrochloric acid, sulfuric acid and nitric acid; organic acids such as formic acid, acetic acid, propionic acid, trifluoroacetic acid and benzoic acid; and sulfonic acids such as methanesulfonic acid and trifluoromethanesulfonic acid. The amount of the acid used is usually selected as appropriate from the range of a 1- to 10-fold molar amount relative to the compound represented by the general formula (2-b). In some cases, the acid can be used to serve as the solvent as well.

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (2-b).

The reaction temperature is usually in the range of −10° C. to the boiling point of the inert solvent used. The reaction time varies with the reaction scale and the reaction temperature, but is usually in the range of a few minutes to 48 hours.

After the reaction is completed, the compound of interest is isolated from the post-reaction mixture by the usual method. As needed, recrystallization, column chromatography, etc. can be employed for the purification of the compound of interest.

Production Method at Step [g]

The intermediate represented by the general formula (2) can be produced by halogenating the compound represented by the general formula (2-a) via the Sandmeyer reaction as described in Chem. Rev. 1988, 88, 765, and esterifying the resulting compound in the usual manner.

Production Method of Intermediate Represented by General Formula (3)

[Chem. 9]

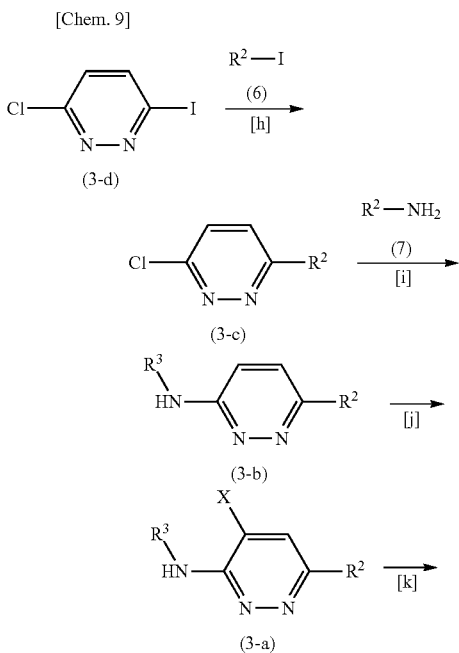

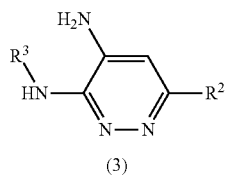

(3)

In the formula, $R^2$, $R^3$ and X are as defined above.

The intermediate represented by the general formula (3) can be produced through the steps [h] to [k] described below.

Step [h]

A step of cross-coupling the compound represented by the general formula (3-d) with the compound represented by the general formula (6), for producing the compound represented by the general formula (3-c).

Step [i]

A step of reacting the compound represented by the general formula (3-c) with the compound represented by the general formula (7), for producing the compound represented by the general formula (3-b).

Step [j]

A step of halogenating the compound represented by the general formula (3-b), for producing the compound represented by the general formula (3-a).

Step [k]

A step of reacting the compound represented by the general formula (3-a) with ammonia in the presence of a catalyst, for producing the intermediate represented by the general formula (3).

Production Method at Step [h]

The compound of the general formula (3-d) produced by the method described in the literature (Tetrahedron, 1999, 55, 15067) is cross-coupled with the compound represented by the general formula (6) in the presence of a metal catalyst, a base and an inert solvent according to the method described in the literature (Journal of Synthetic Organic Chemistry, Japan, vol. 69, No. 7, 2011; Chem. Rev. 2011, 4475; and WO 2013/018928), thus producing the compound represented by the general formula (3-c).

The catalyst used in this reaction may be a palladium compound, including usually available zerovalent or divalent palladium metals and their salts (including their complexes). Such a palladium compound may be supported on activated carbon etc. Preferable examples of the palladium compound include palladium(0)/carbon, palladium(II) acetate, palladium(II) chloride, bis(triphenylphosphine)palladium(II) chloride and tetrakis(triphenylphosphine)palladium(0). The amount of the catalyst used is usually selected as appropriate from the range of a 0.0001- to 1-fold molar amount relative to the compound represented by the general formula (3-d).

For the reaction at this step, the above-mentioned catalyst can be used with a ligand. Examples of the ligand include phosphine ligands such as triphenylphosphine (PPh$_3$), methyldiphenylphosphine (Ph$_2$PCH$_3$), trifurylphosphine (P(2-furyl)$_3$), tri(o-tolyl)phosphine (P(o-tol)$_3$), tri(cyclohexyl)phosphine (PCy$_3$), dicyclohexylphenylphosphine (PhPCy$_2$), tri (t-butyl)phosphine (PtBu$_3$), 2,2'-bis(diphenylphosphino)-1, 1'-binaphthyl (BINAP), diphenylphosphinoferrocene (DPPF), 1,1'-bis(di-t-butylphosphino)ferrocene (DtBPF), N,N-dimethyl-1-[2-(diphenylphosphino)ferrocenyl]ethylamine, 1-[2-(diphenylphosphino)ferrocenyl]ethyl methyl ether and Xantphos; and phosphine mimic ligands such as imidazol-2-ylidene carbene (see Angewandte Chemie International Edition in English, vol. 36, p. 2163 (1997)). The amount of the ligand used is usually selected as appropriate from the range of a 1- to 5-fold molar amount relative to the catalyst used in this reaction.

Examples of the base that can be used in the present invention include hydroxides such as lithium hydroxide, sodium hydroxide and potassium hydroxide; carbonates such as lithium carbonate, lithium hydrogen carbonate, sodium carbonate, sodium hydrogen carbonate, potassium carbonate, potassium hydrogen carbonate and cesium carbonate; acetates such as lithium acetate, sodium acetate and potassium acetate; alkoxides such as sodium methoxide, sodium ethoxide and potassium tert-butoxide; metal hydrides such as sodium hydride and potassium hydride; and organic bases such as pyridine, picoline, lutidine, triethylamine, tributylamine and diisopropylethylamine. The amount of the base used is usually selected as appropriate from the range of a 1- to 5.0-fold molar amount relative to the compound represented by the general formula (3-d).

The reaction temperature is usually in the range of about 0° C. to the boiling point of the solvent used. The reaction time varies with the reaction scale, the reaction temperature and the like, but is usually selected as appropriate from the range of a few minutes to 48 hours.

Production Method at Step [i]

The compound represented by the general formula (3-b) can be produced by reacting the compound represented by the general formula (3-c) with the compound represented by the general formula (7).

The inert solvent used in this reaction may be any solvent that does not markedly inhibit the progress of the reaction, and the examples include aromatic hydrocarbons such as benzene, toluene and xylene; halogenated hydrocarbons such as methylene chloride, chloroform and carbon tetrachloride; halogenated aromatic hydrocarbons such as chlorobenzene and dichlorobenzene; straight-chain or cyclic ethers such as diethyl ether, methyl tert-butyl ether, dioxane and tetrahydrofuran; esters such as ethyl acetate; amides such as dimethylformamide and dimethylacetamide; ketones such as acetone and methyl ethyl ketone; and polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (3-c).

If needed, a base may be used, and examples of the base used include inorganic bases such as sodium hydroxide, potassium hydroxide, sodium carbonate, potassium carbonate, sodium hydrogen carbonate and potassium hydrogen carbonate; acetates such as sodium acetate and potassium acetate; alkali metal alkoxides such as potassium t-butoxide, sodium methoxide and sodium ethoxide; tertiary amines such as triethylamine, diisopropylethylamine and 1,8-diazabicyclo[5.4.0]undec-7-ene; and nitrogen-containing aromatic compounds such as pyridine and dimethylaminopyridine. The amount of the base used is usually in the range of a 1- to 10-fold molar amount relative to the compound represented by the general formula (3-c).

The reaction temperature is usually selected as appropriate from the range of −10° C. to the reflux temperature of the inert solvent used. The reaction time varies with the reaction scale, the reaction temperature and the like and is not the same in every case, but is usually selected as appropriate from the range of a few minutes to 48 hours. The amount of the compound represented by the general formula (7) is usually selected as appropriate from the range of a 1- to 5-fold molar amount relative to the compound represented by the general formula (3-c).

After the reaction is completed, the compound of interest is isolated from the post-reaction mixture by the usual method. As needed, recrystallization, column chromatography, etc. can be employed for the purification of the compound of interest.

Production Method at Step [j]

The compound represented by the general formula (3-a) can be produced by reacting the compound represented by the general formula (3-b) with a halogenating agent.

The inert solvent used in this reaction may be any solvent that does not markedly inhibit the reaction, and the examples include alcohols such as methanol, ethanol, propanol, butanol and 2-propanol; straight-chain or cyclic ethers such as diethyl ether, tetrahydrofuran and dioxane; aromatic hydrocarbons such as benzene, toluene and xylene; esters such as ethyl acetate; and polar solvents such as N,N-dimethylformamide, N,N-dimethylacetamide, 1,3-dimethyl-2-imidazolidinone, water and acetic acid. One of these inert solvents may be used alone, and also two or more of them may be used as a mixture. The amount of the inert solvent used is usually selected as appropriate from the range of 0.1 to 100 L relative to 1 mol of the compound represented by the general formula (3-b).

Examples of the halogenating agent used in the reaction include halogen molecules such as a chlorine, bromine or iodine molecule; halosuccinimides such as NCS and NBS; halogenated hydantoins such as DIH; and thionyl chloride. The amount of the halogenating agent used is usually selected as appropriate from the range of a 1- to 2-fold molar amount relative to the compound represented by the general formula (3-b).

The reaction temperature is usually selected as appropriate from the range of −30° C. to the reflux temperature of the inert solvent used. The reaction time varies with the reaction scale, the reaction temperature and the like and is not the same in every case, but is usually selected as appropriate from the range of a few minutes to 48 hours. After the reaction is completed, the compound of interest is isolated from the post-reaction mixture by the usual method. As needed, recrystallization, column chromatography, etc. can be employed for the purification of the compound of interest.

Production Method at Step [k]

The intermediate represented by the general formula (3) can be produced by reacting the compound represented by the general formula (3-a) with ammonia in the presence of a copper catalyst and a solvent.

The inert solvent used in this reaction may be any solvent that does not markedly inhibit the progress of the reaction, and the examples include alcohols such as methanol, ethanol, propanol, butanol and 2-propanol; aromatic hydrocarbons such as benzene, toluene and xylene; halogenated aromatic hydrocarbons such as chlorobenzene and dichlorobenzene; straight-chain or cyclic ethers such as diethyl ether, methyl tert-butyl ether, dioxane and tetrahydrofuran; amides such as dimethylformamide, dimethylacetamide and N-methylpyrrolidone; and polar solvents such as dimethyl sulfoxide and 1,3-dimethyl-2-imidazolidinone. One of these inert solvents may be used alone, and also two or more of them may be used as a mixture. The amount of the inert solvent used is usually selected as appropriate from the range of 0.1 to 100 L relative to 1 mol of the compound represented by the general formula (3-a).

The copper catalyst used in this reaction can be copper oxide, copper bromide, copper chloride or the like. The amount of the copper catalyst used is usually selected as appropriate from the range of a 1- to 5-fold molar amount relative to the compound represented by the general formula (3-a).

The reaction temperature is usually selected as appropriate from the range of −10° C. to the reflux temperature of the inert solvent used. The reaction time varies with the reaction scale, the reaction temperature and the like and is not the same in every case, but is usually selected as appropriate from the range of a few minutes to 48 hours. The amount of the ammonia used is usually selected as appropriate from the range of a 1- to 5-fold molar amount relative to the compound represented by the general formula (3-a). For efficient progress of the reaction, an autoclave can be used. After the reaction is completed, the compound of interest is isolated from the post-reaction mixture by the usual method. As needed, recrystallization, column chromatography, etc. can be employed for the purification of the compound of interest.

Specific examples of the compound of the present invention are shown below. In the following tables, Me stands for a methyl group, Et stands for an ethyl group, n-Pr stands for a n-propyl group, i-Pr stands for an isopropyl group, c-Pr stands for a cyclopropyl group, n-Bu stands for a n-butyl group, i-Bu stands for an isobutyl group, t-Bu stands for a tert-butyl group, c-Bu stands for a cyclobutyl group, and Ph stands for a phenyl group. Shown in the column of "Physical property" is a melting point (° C.).

[Chem. 10]

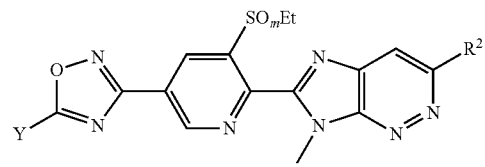

(1a-1)

TABLE 1

| Compound No. | $R^2$ | Y | m | Physical property value |
|---|---|---|---|---|
| 1-1 | $CF_3$ | H | 2 | |
| 1-2 | $CF_3$ | Me | 2 | 208-209 |
| 1-3 | $CF_3$ | Et | 2 | |
| 1-4 | $CF_3$ | i-Pr | 2 | |
| 1-5 | $CF_3$ | n-Pr | 2 | |
| 1-6 | $CF_3$ | c-Pr | 2 | 192-194 |
| 1-7 | $CF_3$ | n-Bu | 2 | |
| 1-8 | $CF_3$ | c-Bu | 2 | |
| 1-9 | $CF_3$ | t-Bu | 2 | |
| 1-10 | $CF_3$ | i-Bu | 2 | |
| 1-11 | $CF_3$ | Cl | 2 | |
| 1-12 | $CF_3$ | Br | 2 | |
| 1-13 | $CF_3$ | $CF_3$ | 2 | |
| 1-14 | $CF_3$ | $CH_2CF_3$ | 2 | |
| 1-15 | $CF_3$ | CN | 2 | |
| 1-16 | $CF_3$ | OH | 2 | |
| 1-17 | $CF_3$ | OMe | 2 | |
| 1-18 | $CF_3$ | OEt | 2 | |
| 1-19 | $CF_3$ | $OCH_2C\equiv CH$ | 2 | |
| 1-20 | $CF_3$ | $OCH_2CN$ | 2 | |
| 1-21 | $CF_3$ | $OCH_2CF_3$ | 2 | |
| 1-22 | $CF_3$ | $NH_2$ | 2 | |
| 1-23 | $CF_3$ | NHMe | 2 | |
| 1-24 | $CF_3$ | $NMe_2$ | 2 | |
| 1-25 | $CF_3$ | $CO_2Me$ | 2 | |

TABLE 1-continued

| Compound No. | $R^2$ | Y | m | Physical property value |
|---|---|---|---|---|
| 1-26 | $CF_3$ | $CO_2Et$ | 2 | |
| 1-27 | $CF_3$ | $CONH_2$ | 2 | |
| 1-28 | $CF_3$ | Ph | 2 | |

TABLE 2

| Compound No. | $R^2$ | Y | m | Physical property value |
|---|---|---|---|---|
| 1-29 | $CF_2CF_3$ | H | 2 | 234-235 |
| 1-30 | $CF_2CF_3$ | Me | 2 | 185-186 |
| 1-31 | $CF_2CF_3$ | Et | 2 | |
| 1-32 | $CF_2CF_3$ | i-Pr | 2 | |
| 1-33 | $CF_2CF_3$ | n-Pr | 2 | |
| 1-34 | $CF_2CF_3$ | c-Pr | 2 | 154-155 |
| 1-35 | $CF_2CF_3$ | n-Bu | 2 | |
| 1-36 | $CF_2CF_3$ | c-Bu | 2 | |
| 1-37 | $CF_2CF_3$ | t-Bu | 2 | |
| 1-38 | $CF_2CF_3$ | i-Bu | 2 | |
| 1-39 | $CF_2CF_3$ | Cl | 2 | |
| 1-40 | $CF_2CF_3$ | Br | 2 | |
| 1-41 | $CF_2CF_3$ | $CF_3$ | 2 | 177-178 |
| 1-42 | $CF_2CF_3$ | $CH_2CF_3$ | 2 | 183-184 |
| 1-43 | $CF_2CF_3$ | CN | 2 | |
| 1-44 | $CF_2CF_3$ | OH | 2 | |
| 1-45 | $CF_2CF_3$ | OMe | 2 | |
| 1-46 | $CF_2CF_3$ | OEt | 2 | |
| 1-47 | $CF_2CF_3$ | $OCH_2C{\equiv}CH$ | 2 | |
| 1-48 | $CF_2CF_3$ | $OCH_2CN$ | 2 | |
| 1-49 | $CF_2CF_3$ | $OCH_2CF_3$ | 2 | |
| 1-50 | $CF_2CF_3$ | $NH_2$ | 2 | |
| 1-51 | $CF_2CF_3$ | NHMe | 2 | |
| 1-52 | $CF_2CF_3$ | $NMe_2$ | 2 | |
| 1-53 | $CF_2CF_3$ | $CO_2Me$ | 2 | |
| 1-54 | $CF_2CF_3$ | $CO_2Et$ | 2 | |
| 1-55 | $CF_2CF_3$ | $CONH_2$ | 2 | |
| 1-56 | $CF_2CF_3$ | Ph | 2 | 160-161 |

TABLE 3

| Compound No. | $R^2$ | Y | m | Physical property value |
|---|---|---|---|---|
| 1-57 | $OCH_2CF_3$ | H | 2 | |
| 1-58 | $OCH_2CF_3$ | Me | 2 | |
| 1-59 | $OCH_2CF_3$ | Et | 2 | |
| 1-60 | $OCH_2CF_3$ | i-Pr | 2 | |
| 1-61 | $OCH_2CF_3$ | n-Pr | 2 | |
| 1-62 | $OCH_2CF_3$ | c-Pr | 2 | 163-164 |
| 1-63 | $OCH_2CF_3$ | n-Bu | 2 | |
| 1-64 | $OCH_2CF_3$ | c-Bu | 2 | |
| 1-65 | $OCH_2CF_3$ | t-Bu | 2 | |
| 1-66 | $OCH_2CF_3$ | i-Bu | 2 | |
| 1-67 | $OCH_2CF_3$ | Cl | 2 | |
| 1-68 | $OCH_2CF_3$ | Br | 2 | |
| 1-69 | $OCH_2CF_3$ | $CF_3$ | 2 | |
| 1-70 | $OCH_2CF_3$ | $CH_2CF_3$ | 2 | |
| 1-71 | $OCH_2CF_3$ | CN | 2 | |
| 1-72 | $OCH_2CF_3$ | OH | 2 | |
| 1-73 | $OCH_2CF_3$ | OMe | 2 | |
| 1-74 | $OCH_2CF_3$ | OEt | 2 | |
| 1-75 | $OCH_2CF_3$ | $OCH_2C{\equiv}CH$ | 2 | |
| 1-76 | $OCH_2CF_3$ | $OCH_2CN$ | 2 | |
| 1-77 | $OCH_2CF_3$ | $OCH_2CF_3$ | 2 | |
| 1-78 | $OCH_2CF_3$ | $NH_2$ | 2 | |
| 1-79 | $OCH_2CF_3$ | NHMe | 2 | |
| 1-80 | $OCH_2CF_3$ | $NMe_2$ | 2 | |
| 1-81 | $OCH_2CF_3$ | $CO_2Me$ | 2 | |
| 1-82 | $OCH_2CF_3$ | $CO_2Et$ | 2 | |

TABLE 3-continued

| Compound No. | $R^2$ | Y | m | Physical property value |
|---|---|---|---|---|
| 1-83 | $OCH_2CF_3$ | $CONH_2$ | 2 | |
| 1-84 | $OCH_2CF_3$ | Ph | 2 | |

TABLE 4

| Compound No. | $R^2$ | Y | m | Physical property value |
|---|---|---|---|---|
| 1-85 | $OCHF_2$ | H | 2 | |
| 1-86 | $OCHF_2$ | Me | 2 | |
| 1-87 | $OCHF_2$ | Et | 2 | |
| 1-88 | $OCHF_2$ | i-Pr | 2 | |
| 1-89 | $OCHF_2$ | n-Pr | 2 | |
| 1-90 | $OCHF_2$ | c-Pr | 2 | |
| 1-91 | $OCHF_2$ | n-Bu | 2 | |
| 1-92 | $OCHF_2$ | c-Bu | 2 | |
| 1-93 | $OCHF_2$ | t-Bu | 2 | |
| 1-94 | $OCHF_2$ | i-Bu | 2 | |
| 1-95 | $OCHF_2$ | Cl | 2 | |
| 1-96 | $OCHF_2$ | Br | 2 | |
| 1-97 | $OCHF_2$ | $CF_3$ | 2 | |
| 1-98 | $OCHF_2$ | $CH_2CF_3$ | 2 | |
| 1-99 | $OCHF_2$ | CN | 2 | |
| 1-100 | $OCHF_2$ | OH | 2 | |
| 1-101 | $OCHF_2$ | OMe | 2 | |
| 1-102 | $OCHF_2$ | OEt | 2 | |
| 1-103 | $OCHF_2$ | $OCH_2C{\equiv}CH$ | 2 | |
| 1-104 | $OCHF_2$ | $OCH_2CN$ | 2 | |
| 1-105 | $OCHF_2$ | $OCH_2CF_3$ | 2 | |
| 1-106 | $OCHF_2$ | $NH_2$ | 2 | |
| 1-107 | $OCHF_2$ | NHMe | 2 | |
| 1-108 | $OCHF_2$ | $NMe_2$ | 2 | |
| 1-109 | $OCHF_2$ | $CO_2Me$ | 2 | |
| 1-110 | $OCHF_2$ | $CO_2Et$ | 2 | |
| 1-111 | $OCHF_2$ | $CONH_2$ | 2 | |
| 1-112 | $OCHF_2$ | Ph | 2 | |

TABLE 5

| Compound No. | $R^2$ | Y | m | Physical property value |
|---|---|---|---|---|
| 1-113 | $SCF_3$ | H | 2 | |
| 1-114 | $SCF_3$ | Me | 2 | |
| 1-115 | $SCF_3$ | Et | 2 | |
| 1-116 | $SCF_3$ | i-Pr | 2 | |
| 1-117 | $SCF_3$ | n-Pr | 2 | |
| 1-118 | $SCF_3$ | c-Pr | 2 | |
| 1-119 | $SCF_3$ | n-Bu | 2 | |
| 1-120 | $SCF_3$ | c-Bu | 2 | |
| 1-121 | $SCF_3$ | t-Bu | 2 | |
| 1-122 | $SCF_3$ | i-Bu | 2 | |
| 1-123 | $SCF_3$ | Cl | 2 | |
| 1-124 | $SCF_3$ | Br | 2 | |
| 1-125 | $SCF_3$ | $CF_3$ | 2 | |
| 1-126 | $SCF_3$ | $CH_2CF_3$ | 2 | |
| 1-127 | $SCF_3$ | CN | 2 | |
| 1-128 | $SCF_3$ | OH | 2 | |
| 1-129 | $SCF_3$ | OMe | 2 | |
| 1-130 | $SCF_3$ | OEt | 2 | |
| 1-131 | $SCF_3$ | $OCH_2C{\equiv}CH$ | 2 | |
| 1-132 | $SCF_3$ | $OCH_2CN$ | 2 | |
| 1-133 | $SCF_3$ | $OCH_2CF_3$ | 2 | |
| 1-134 | $SCF_3$ | $NH_2$ | 2 | |
| 1-135 | $SCF_3$ | NHMe | 2 | |
| 1-136 | $SCF_3$ | $NMe_2$ | 2 | |
| 1-137 | $SCF_3$ | $CO_2Me$ | 2 | |
| 1-138 | $SCF_3$ | $CO_2Et$ | 2 | |

TABLE 5-continued

| Compound No. | R² | Y | m | Physical property value |
|---|---|---|---|---|
| 1-139 | SCF₃ | CONH₂ | 2 | |
| 1-140 | SCF₃ | Ph | 2 | |

[Chem. 11]

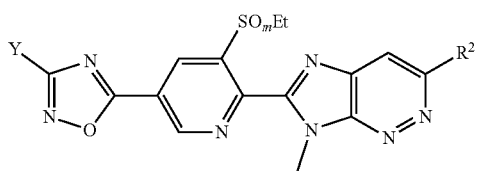

(1b-1)

TABLE 6

| Compound No. | R² | Y | m | Physical property value |
|---|---|---|---|---|
| 2-1 | CF₃ | H | 2 | |
| 2-2 | CF₃ | Me | 2 | |
| 2-3 | CF₃ | Et | 2 | |
| 2-4 | CF₃ | i-Pr | 2 | |
| 2-5 | CF₃ | n-Pr | 2 | |
| 2-6 | CF₃ | c-Pr | 2 | |
| 2-7 | CF₃ | n-Bu | 2 | |
| 2-8 | CF₃ | c-Bu | 2 | |
| 2-9 | CF₃ | t-Bu | 2 | |
| 2-10 | CF₃ | i-Bu | 2 | |
| 2-11 | CF₃ | Cl | 2 | |
| 2-12 | CF₃ | Br | 2 | |
| 2-13 | CF₃ | CF₃ | 2 | |
| 2-14 | CF₃ | CH₂CF₃ | 2 | |
| 2-15 | CF₃ | CN | 2 | |
| 2-16 | CF₃ | OH | 2 | |
| 2-17 | CF₃ | OMe | 2 | |
| 2-18 | CF₃ | OEt | 2 | |
| 2-19 | CF₃ | OCH₂C≡CH | 2 | |
| 2-20 | CF₃ | OCH₂CN | 2 | |
| 2-21 | CF₃ | OCH₂CF₃ | 2 | |
| 2-22 | CF₃ | NH₂ | 2 | |
| 2-23 | CF₃ | NHMe | 2 | |
| 2-24 | CF₃ | NMe₂ | 2 | |
| 2-25 | CF₃ | CO₂Me | 2 | |
| 2-26 | CF₃ | CO₂Et | 2 | |
| 2-27 | CF₃ | CONH₂ | 2 | |
| 2-28 | CF₃ | Ph | 2 | |

TABLE 7

| Compound No. | R² | Y | m | Physical property value |
|---|---|---|---|---|
| 2-29 | CF₂CF₃ | H | 2 | |
| 2-30 | CF₂CF₃ | Me | 2 | |
| 2-31 | CF₂CF₃ | Et | 2 | |
| 2-32 | CF₂CF₃ | i-Pr | 2 | |
| 2-33 | CF₂CF₃ | n-Pr | 2 | |
| 2-34 | CF₂CF₃ | c-Pr | 2 | |
| 2-35 | CF₂CF₃ | n-Bu | 2 | |
| 2-36 | CF₂CF₃ | c-Bu | 2 | |
| 2-37 | CF₂CF₃ | t-Bu | 2 | |
| 2-38 | CF₂CF₃ | i-Bu | 2 | |
| 2-39 | CF₂CF₃ | Cl | 2 | |

TABLE 7-continued

| Compound No. | R² | Y | m | Physical property value |
|---|---|---|---|---|
| 2-40 | CF₂CF₃ | Br | 2 | |
| 2-41 | CF₂CF₃ | CF₃ | 2 | |
| 2-42 | CF₂CF₃ | CH₂CF₃ | 2 | |
| 2-43 | CF₂CF₃ | CN | 2 | |
| 2-44 | CF₂CF₃ | OH | 2 | |
| 2-45 | CF₂CF₃ | OMe | 2 | |
| 2-46 | CF₂CF₃ | OEt | 2 | |
| 2-47 | CF₂CF₃ | OCH₂C≡CH | 2 | |
| 2-48 | CF₂CF₃ | OCH₂CN | 2 | |
| 2-49 | CF₂CF₃ | OCH₂CF₃ | 2 | |
| 2-50 | CF₂CF₃ | NH₂ | 2 | |
| 2-51 | CF₂CF₃ | NHMe | 2 | |
| 2-52 | CF₂CF₃ | NMe₂ | 2 | |
| 2-53 | CF₂CF₃ | CO₂Me | 2 | |
| 2-54 | CF₂CF₃ | CO₂Et | 2 | |
| 2-55 | CF₂CF₃ | CONH₂ | 2 | |
| 2-56 | CF₂CF₃ | Ph | 2 | 171-172 |

TABLE 8

| Compound No. | R² | Y | m | Physical property value |
|---|---|---|---|---|
| 2-57 | OCH₂CF₃ | H | 2 | |
| 2-58 | OCH₂CF₃ | Me | 2 | |
| 2-59 | OCH₂CF₃ | Et | 2 | |
| 2-60 | OCH₂CF₃ | i-Pr | 2 | |
| 2-61 | OCH₂CF₃ | n-Pr | 2 | |
| 2-62 | OCH₂CF₃ | c-Pr | 2 | |
| 2-63 | OCH₂CF₃ | n-Bu | 2 | |
| 2-64 | OCH₂CF₃ | c-Bu | 2 | |
| 2-65 | OCH₂CF₃ | t-Bu | 2 | |
| 2-66 | OCH₂CF₃ | i-Bu | 2 | |
| 2-67 | OCH₂CF₃ | Cl | 2 | |
| 2-68 | OCH₂CF₃ | Br | 2 | |
| 2-69 | OCH₂CF₃ | CF₃ | 2 | |
| 2-70 | OCH₂CF₃ | CH₂CF₃ | 2 | |
| 2-71 | OCH₂CF₃ | CN | 2 | |
| 2-72 | OCH₂CF₃ | OH | 2 | |
| 2-73 | OCH₂CF₃ | OMe | 2 | |
| 2-74 | OCH₂CF₃ | OEt | 2 | |
| 2-75 | OCH₂CF₃ | OCH₂C≡CH | 2 | |
| 2-76 | OCH₂CF₃ | OCH₂CN | 2 | |
| 2-77 | OCH₂CF₃ | OCH₂CF₃ | 2 | |
| 2-78 | OCH₂CF₃ | NH₂ | 2 | |
| 2-79 | OCH₂CF₃ | NHMe | 2 | |
| 2-80 | OCH₂CF₃ | NMe₂ | 2 | |
| 2-81 | OCH₂CF₃ | CO₂Me | 2 | |
| 2-82 | OCH₂CF₃ | CO₂Et | 2 | |
| 2-83 | OCH₂CF₃ | CONH₂ | 2 | |
| 2-84 | OCH₂CF₃ | Ph | 2 | |

TABLE 9

| Compound No. | R² | Y | m | Physical property value |
|---|---|---|---|---|
| 2-85 | OCHF₂ | H | 2 | |
| 2-86 | OCHF₂ | Me | 2 | |
| 2-87 | OCHF₂ | Et | 2 | |
| 2-88 | OCHF₂ | i-Pr | 2 | |
| 2-89 | OCHF₂ | n-Pr | 2 | |
| 2-90 | OCHF₂ | c-Pr | 2 | |
| 2-91 | OCHF₂ | n-Bu | 2 | |
| 2-92 | OCHF₂ | c-Bu | 2 | |
| 2-93 | OCHF₂ | t-Bu | 2 | |
| 2-94 | OCHF₂ | i-Bu | 2 | |
| 2-95 | OCHF₂ | Cl | 2 | |
| 2-96 | OCHF₂ | Br | 2 | |

TABLE 9-continued

| Compound No. | R² | Y | m | Physical property value |
|---|---|---|---|---|
| 2-97 | OCHF₂ | CF₃ | 2 | |
| 2-98 | OCHF₂ | CH₂CF₃ | 2 | |
| 2-99 | OCHF₂ | CN | 2 | |
| 2-100 | OCHF₂ | OH | 2 | |
| 2-101 | OCHF₂ | OMe | 2 | |
| 2-102 | OCHF₂ | OEt | 2 | |
| 2-103 | OCHF₂ | OCH₂C≡CH | 2 | |
| 2-104 | OCHF₂ | OCH₂CN | 2 | |
| 2-105 | OCHF₂ | OCH₂CF₃ | 2 | |
| 2-106 | OCHF₂ | NH₂ | 2 | |
| 2-107 | OCHF₂ | NHMe | 2 | |
| 2-108 | OCHF₂ | NMe₂ | 2 | |
| 2-109 | OCHF₂ | CO₂Me | 2 | |
| 2-110 | OCHF₂ | CO₂Et | 2 | |
| 2-111 | OCHF₂ | CONH₂ | 2 | |
| 2-112 | OCHF₂ | Ph | 2 | |

TABLE 10

| Compound No. | R² | Y | m | Physical property value |
|---|---|---|---|---|
| 2-113 | SCF₃ | H | 2 | |
| 2-114 | SCF₃ | Me | 2 | |
| 2-115 | SCF₃ | Et | 2 | |
| 2-116 | SCF₃ | i-Pr | 2 | |
| 2-117 | SCF₃ | n-Pr | 2 | |
| 2-118 | SCF₃ | c-Pr | 2 | |
| 2-119 | SCF₃ | n-Bu | 2 | |
| 2-120 | SCF₃ | c-Bu | 2 | |
| 2-121 | SCF₃ | t-Bu | 2 | |
| 2-122 | SCF₃ | i-Bu | 2 | |
| 2-123 | SCF₃ | Cl | 2 | |
| 2-124 | SCF₃ | Br | 2 | |
| 2-125 | SCF₃ | CF₃ | 2 | |
| 2-126 | SCF₃ | CH₂CF₃ | 2 | |
| 2-127 | SCF₃ | CN | 2 | |
| 2-128 | SCF₃ | OH | 2 | |
| 2-129 | SCF₃ | OMe | 2 | |
| 2-130 | SCF₃ | OEt | 2 | |
| 2-131 | SCF₃ | OCH₂C≡CH | 2 | |
| 2-132 | SCF₃ | OCH₂CN | 2 | |
| 2-133 | SCF₃ | OCH₂CF₃ | 2 | |
| 2-134 | SCF₃ | NH₂ | 2 | |
| 2-135 | SCF₃ | NHMe | 2 | |
| 2-136 | SCF₃ | NMe₂ | 2 | |
| 2-137 | SCF₃ | CO₂Me | 2 | |
| 2-138 | SCF₃ | CO₂Et | 2 | |
| 2-139 | SCF₃ | CONH₂ | 2 | |
| 2-140 | SCF₃ | Ph | 2 | |

The agricultural and horticultural insecticide comprising the heterocycle-bound condensed heterocyclic compound represented by the general formula (1) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, nematodes, etc.

Specific examples of the pests, nematodes, etc. include the following:

the species of the order Lepidoptera such as *Parasa consocia*, *Anomis mesogona*, *Papilio xuthus*, *Matsumuraeses azukivora*, *Ostrinia scapulalis*, *Spodoptera exempta*, *Hyphantria cunea*, *Ostrinia furnacalis*, *Pseudaletia separata*, *Tinea translucens*, *Bactra furfurana*, *Parnara guttata*, *Marasmia exigua*, *Parnara guttata*, *Sesamia inferens*, *Brachmia triannulella*, *Monema flavescens*, *Trichoplusia ni*, *Pleuroptya ruralis*, *Cystidia couaggaria*, *Lampides boeticus*, *Cephonodes hylas*, *Helicoverpa armigera*, *Phalerodonta manleyi*, *Eumeta japonica*, *Pieris brassicae*, *Malacosoma neustria testacea*, *Stathmopoda masinissa*, *Cuphodes diospyrosella*, *Archips xylosteanus*, *Agrotis segetum*, *Tetramoera schistaceana*, *Papilio machaon hippocrates*, *Endoclyta sinensis*, *Lyonetia prunifoliella*, *Phyllonorycter ringoneella*, *Cydia kurokoi*, *Eucoenogenes aestuosa*, *Lobesia botrana*, *Latoia sinica*, *Euzophera batangensis*, *Phalonidia mesotypa*, *Spilosoma imparilis*, *Glyphodes pyloalis*, *Olethreutes mori*, *Tineola bisselliella*, *Endoclyta excrescens*, *Nemapogon granellus*, *Synanthedon hector*, *Cydia pomonella*, *Plutella xylostella*, *Cnaphalocrocis medinalis*, *Sesamia calamistis*, *Scirpophaga incertulas*, *Pediasia teterrellus*, *Phthorimaea operculella*, *Stauropus fagi persimilis*, *Etiella zinckenella*, *Spodoptera exigua*, *Palpifer sexnotata*, *Spodoptera mauritia*, *Scirpophaga innotata*, *Xestia c-nigrum*, *Spodoptera depravata*, *Ephestia kuehniella*, *Angerona prunaria*, *Clostera anastomosis*, *Pseudoplusia includens*, *Matsumuraeses falcana*, *Helicoverpa assulta*, *Autographa nigrisigna*, *Agrotis ipsilon*, *Euproctis pseudoconspersa*, *Adoxophyes orana*, *Caloptilia theivora*, *Homona magnanima*, *Ephestia elutella*, *Eumeta minuscula*, *Clostera anachoreta*, *Heliothis maritima*, *Sparganothis pilleriana*, *Busseola fusca*, *Euproctis subflava*, *Biston robustum*, *Heliothis zea*, *Aedia leucomelas*, *Narosoideus flavidorsalis*, *Viminia rumicis*, *Bucculatrix pyrivorella*, *Grapholita molesta*, *Spulerina astaurota*, *Ectomyelois pyrivorella*, *Chilo suppressalis*, *Acrolepiopsis sapporensis*, *Plodia interpunctella*, *Hellula undalis*, *Sitotroga cerealella*, *Spodoptera litura*, a species of the family Tortricidae (*Eucosma aporema*), *Acleris comariana*, *Scopelodes contractus*, *Orgyia thyellina*, *Spodoptera frugiperda*, *Ostrinia zaguliaevi*, *Naranga aenescens*, *Andraca bipunctata*, *Paranthrene regalis*, *Acosmeryx castanea*, *Phyllocnistis toparcha*, *Endopiza viteana*, *Eupoecillia ambiguella*, *Anticarsia gemmatalis*, *Cnephasia cinereipalpana*, *Lymantria dispar*, *Dendrolimus spectabilis*, *Leguminivora glycinivorella*, *Maruca testulalis*, *Matsumuraeses phaseoli*, *Caloptilia soyella*, *Phyllocnistis citrella*, *Omiodes indicata*, *Archips fuscocupreanus*, *Acanthoplusia agnata*, *Bambalina* sp., *Carposina niponensis*, *Conogethes punctiferalis*, *Synanthedon* sp., *Lyonetia clerkella*, *Papilio helenus*, *Colias erate poliographus*, *Phalera flavescens*, the species of the family Pieridae such as *Pieris rapae crucivora* and *Pieris rapae*, *Euproctis similis*, *Acrolepiopsis suzukiella*, *Ostrinia nubilalis*, *Mamestra brassicae*, *Ascotis selenaria*, *Phtheochroides clandestina*, *Hoshinoa adumbratana*, *Odonestis pruni japonensis*, *Triaena intermedia*, *Adoxophyes orana fasciata*, *Grapholita inopinata*, *Spilonota ocellana*, *Spilonota lechriaspis*, *Illiberis pruni*, *Argyresthia conjugella*, *Caloptilia zachrysa*, *Archips breviplicanus*, *Anomis flava*, *Pectinophora gossypiella*, *Notarcha derogata*, *Diaphania indica*, *Heliothis virescens* and *Earias cupreoviridis*;

the species of the order Hemiptera such as *Nezara antennata*, *Stenotus rubrovittatus*, *Graphosoma rubrolineatum*, *Trigonotylus coelestialium*, *Aeschynteles maculatus*, *Creontiades pallidifer*, *Dysdercus cingulatus*, *Chrysomphalus ficus*, *Aonidiella aurantii*, *Graptopsaltria nigrofuscata*, *Blissus leucopterus*, *Icerya purchasi*, *Piezodorus hybneri*, *Lagynotomus elongatus*, *Thaia subrufa*, *Scotinophara lurida*, *Sitobion ibarae*, *Stariodes iwasakii*, *Aspidiotus destructor*, *Taylorilygus pallidulus*, *Myzus mumecola*, *Pseudaulacaspis prunicola*, *Acyrthosiphon pisum*, *Anacanthocoris striicornis*, *Ectometopterus micantulus*, *Eysarcoris lewisi*, *Molipteryx fuliginosa*, *Cicadella viridis*, *Rhopalosiphum rufiabdominalis*, *Saissetia oleae*, *Trialeurodes vaporariorum*,

*Aguriahana quercus, Lygus* spp., *Euceraphis punctipennis, Andaspis kashicola, Coccus pseudomagnoliarum, Cavelerius saccharivorus, Galeatus spinifrons, Macrosiphoniella sanborni, Aonidiella citrina, Halyomorpha mista, Stephanitis fasciicarina, Trioza camphorae, Leptocorisa chinensis, Trioza quercicola, Uhlerites latius, Erythroneura comes, Paromius exiguus, Duplaspidiotus claviger, Nephotettix nigropictus, Halticiellus insularis, Perkinsiella saccharicida, Psylla malivorella, Anomomeura mori, Pseudococcus longispinis, Pseudaulacaspis pentagona, Pulvinaria kuwacola, Apolygus lucorum, Togo hemipterus, Toxoptera aurantii, Saccharicoccus sacchari, Geoica lucifuga, Numata muiri, Comstockaspis perniciosa, Unaspis citri, Aulacorthum solani, Eysarcoris ventralis, Bemisia argentifolii, Cicadella spectra, Aspidiotus hederae, Liorhyssus hyalinus, Calophya nigridorsalis, Sogatella furcifera, Megoura crassicauda, Brevicoryne brassicae, Aphis glycines, Leptocorisa oratorius, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glaucias subpunctatus, Orthotylus flavosparsus, Rhopalosiphum maidis, Peregrinus maidis, Eysarcoris parvus, Cimex lectularius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wistariae, Lepholeucaspis japonica, Sappaphis piri, Lipaphis erysimi, Neotoxoptera formosana, Rhopalosiphum nymphaeae, Edwardsiana rosae, Pinnaspis aspidistrae, Psylla alni, Speusotettix subfusculus, Alnetoidia alneti, Sogatella panicicola, Adelphocoris lineolatus, Dysdercus poecilus, Parlatoria ziziphi, Uhlerites debile, Laodelphax striatellus, Eurydema pulchrum, Cletus trigonus, Clovia punctata, Empoasca* spp., *Coccus hesperidum, Pachybrachius luridus, Planococcus kraunhiae, Stenotus binotatus, Arboridia apicalis, Macrosteles fascifrons, Dolycoris baccarum, Adelphocoris triannulatus, Viteus vitifolii, Acanthocoris sordidus, Leptocorisa acuta, Macropes obnubilus, Cletus punctiger, Riptortus clavatus, Paratrioza cockerelli, Aphrophora costalis, Lygus disponsi, Lygus saundersi, Crisicoccus pini, Empoasca abietis, Crisicoccus matsumotoi, Aphis craccivora, Megacopta punctatissimum, Eysarcoris guttiger, Lepidosaphes beckii, Diaphorina citri, Toxoptera citricidus, Planococcus citri, Dialeurodes citri, Aleurocanthus spiniferus, Pseudococcus citriculus, Zyginella citri, Pulvinaria citricola, Coccus discrepans, Pseudaonidia duplex, Pulvinaria aurantii, Lecanium corni, Nezara viridula, Stenodema calcaratum, Rhopalosiphum padi, Sitobion akebiae, Schizaphis graminum, Sorhoanus tritici, Brachycaudus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonuguis mali, Orientus ishidai, Ovatus malicolens, Eriosoma lanigerum, Ceroplastes rubens* and *Aphis gossypii*;

the species of the order Coleoptera such as *Xystrocera globosa, Paederus fuscipes, Eucetonia roelofsi, Callosobruchus chinensis, Cylas formicarius, Hypera postica, Echinocnemus squameus, Oulema oryzae, Donacia provosti, Lissorhoptrus oryzophilus, Colasposoma dauricum, Eucepes postfasciatus, Epilachna varivestis, Acanthoscelides obtectus, Diabrotica virgifera virgifera, Involvulus cupreus, Aulacophora femoralis, Bruchus pisorum, Epilachna vigintioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Carpophilus hemipterus, Oxycetonia jucunda, Diabrotica* spp., *Mimela splendens, Sitophilus zeamais, Tribolium castaneum, Sitophilus oryzae, Palorus subdepressus, Melolontha japonica, Anoplophora malasiaca, Neatus picipes, Leptinotarsa decemlineata, Diabrotica undecimpunctata howardi, Sphenophorus venatus, Crioceris quatuordecimpunctata, Conotrachelus nenuphar, Ceuthorhynchidius albosuturalis, Phaedon brassicae, Lasioderma serricorne, Sitona japonicus, Adoretus tenuimaculatus, Tenebrio molitor, Basilepta balyi, Hypera nigrirostris, Chaetocnema concinna, Anomala cuprea, Heptophylla picea, Epilachna vigintioctopunctata, Diabrotica longicornis, Eucetonia pilifera, Agriotes* spp., *Attagenus unicolor japonicus, Pagria signata, Anomala rufocuprea, Palorus ratzeburgii, Alphitobius laevigatus, Anthrenus verbasci, Lyctus brunneus, Tribolium confusum, Medythia nigrobilineata, Xylotrechus pyrrhoderus, Epitrix cucumeris, Tomicus piniperda, Monochamus alternatus, Popillia japonica, Epicauta gorhami, Sitophilus zeamais, Rhynchites heros, Listroderes costirostris, Callosobruchus maculatus, Phyllobius armatus, Anthonomus pomorum, Linaeidea aenea* and *Anthonomus grandis*;

the species of the order Diptera such as *Culex pipiens pallens, Pegomya hyoscyami, Liriomyza huidobrensis, Musca domestica, Chlorops oryzae, Hydrellia sasakii, Agromyza oryzae, Hydrellia griseola, Hydrellia griseola, Ophiomyia phaseoli, Dacus cucurbitae, Drosophila suzukii, Rhacochlaena japonica, Muscina stabulans*, the species of the family Phoridae such as *Megaselia spiracularis, Clogmia albipunctata, Tipula aino, Phormia regina, Culex tritaeniorhynchus, Anopheles sinensis, Hylemya brassicae, Asphondylia* sp., *Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dorsalis, Dacus tsuneonis, Sitodiplosis mosellana, Meromuza nigriventris, Anastrepha ludens* and *Rhagoletis pomonella*;

the species of the order Hymenoptera such as *Pristomyrmex pungens*, the species of the family Bethylidae, *Monomorium pharaonis, Pheidole noda, Athalia rosae, Dryocosmus kuriphilus, Formica fusca japonica*, the species of the subfamily Vespinae, *Athalia infumata infumata, Arge pagana, Athalia japonica, Acromyrmex* spp., *Solenopsis* spp., *Arge mali* and *Ochetellus glaber*;

the species of the order Orthoptera such as *Homorocoryphus lineosus, Gryllotalpa* sp., *Oxya hyla intricata, Oxya yezoensis, Locusta migratoria, Oxya japonica, Homorocoryphus jezoensis* and *Teleogryllus emma*;

the species of the order Thysanoptera such as *Selenothrips rubrocinctus, Stenchaetothrips biformis, Haplothrips aculeatus, Ponticulothrips diospyrosi, Thrips flavus, Anaphothrips obscurus, Liothrips floridensis, Thrips simplex, Thrips nigropilosus, Heliothrips haemorrhoidalis, Pseudodendrothrips mori, Microcephalothrips abdominalis, Leeuwenia pasanii, Litotetothrips pasaniae, Scirtothrips citri, Haplothrips chinensis, Mycterothrips glycines, Thrips setosus, Scirtothrips dorsalis, Dendrothrips minowai, Haplothrips niger, Thrips tabaci, Thrips alliorum, Thrips hawaiiensis, Haplothrips kurdjumovi, Chirothrips manicatus, Frankliniella intonsa, Thrips coloratus, Frankliniella occidentalis, Thrips palmi, Frankliniella lilivora* and *Liothrips vaneeckei*;

the species of the order Acari such as *Leptotrombidium akamushi, Tetranychus ludeni, Dermacentor variabilis, Tetranychus truncatus, Ornithonyssus bacoti, Demodex canis, Tetranychus viennensis, Tetranychus kanzawai*, the species of the family Ixodidae such as *Rhipicephalus sanguineus, Cheyletus malaccensis, Tyrophagus putrescentiae, Dermatophagoides farinae, Latrodectus hasseltii, Dermacentor taiwanicus, Acaphylla theavagrans, Polyphagotarsonemus latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini* and *Sancassania* sp.;

the species of the order Isoptera such as *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei* and *Reticulitermes speratus*;

the species of the order Blattodea such as *Periplaneta fuliginosa, Blattella germanica, Blatta orientalis, Periplaneta brunnea, Blattella lituricollis, Periplaneta japonica* and *Periplaneta americana*;

the species of the order Siphonaptera such as *Pulex irritans, Ctenocephalides felis* and *Ceratophyllus gallinae*;

the species of the phylum Nematoda such as *Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus* and *Tylenchus semipenetrans*; and the species of the phylum Mollusca such as *Pomacea canaliculata, Achatina fulica, Meghimatium bilineatum, Lehmannina valentiana, Limax flavus* and *Acusta despecta sieboldiana*.

In addition, the agricultural and horticultural insecticide of the present invention has a strong insecticidal effect on *Tuta absoluta* as well.

Further, mites and ticks parasitic on animals are also included in the target pests, and the examples include the species of the family Ixodidae such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus* and *Dermacentor taiwanesis; Dermanyssus gallinae*; the species of the genus *Ornithonyssus* such as *Ornithonyssus sylviarum* and *Ornithonyssus bursa*; the species of the family Trombiculidae such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi* and *Helenicula miyagawai*; the species of the family Cheyletidae such as *Cheyletiella yasguri, Cheyletiella parasitivorax* and *Cheyletiella blakei*; the species of the superfamily Sarcoptoidea such as *Psoroptes cuniculi, Chorioptes bovis, Otodectes cynotis, Sarcoptes scabiei* and *Notoedres cati*; and the species of the family Demodicidae such as *Demodex canis*.

Other target pests include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis, Ctenocephalides felis, Pulex irritans, Echidnophaga gallinacea, Xenopsylla cheopis, Leptopsylla segnis, Nosopsyllus fasciatus* and *Monopsyllus anisus*.

Other target pests include ectoparasites, for example, the species of the suborder Anoplura such as *Haematopinus eurysternus, Haematopinus asini, Dalmalinia ovis, Linognathus vituli, Haematopinus suis, Phthirus pubis* and *Pediculus capitis*; the species of the suborder Mallophaga such as *Trichodectes canis*; and hematophagous Dipteran insect pests such as *Tabanus trigonus, Culicoides schultzei* and *Simulium ornatum*. In addition, examples of endoparasites include nematodes such as lungworms, whipworms, nodular worms, endogastric parasitic worms, ascarides and filarial worms; cestodes such as *Spirometra erinacei, Diphyllobothrium latum, Dipylidium caninum, Multiceps multiceps, Echinococcus granulosus* and *Echinococcus multilocularis*; trematodes such as *Schistosoma japonicum* and *Fasciola hepatica*; and protozoa such as coccidia, *Plasmodium*, intestinal *Sarcocystis, Toxoplasma* and *Cryptosporidium*.

The heterocycle-bound condensed heterocyclic compound represented by the general formula (1) of the present invention or a salt thereof may be internally or externally administered.

The agricultural and horticultural insecticide comprising the heterocycle-bound condensed heterocyclic compound represented by the general formula (1) of the present invention or a salt thereof as an active ingredient has a remarkable control effect on the above-described pests which damage lowland crops, field crops, fruit trees, vegetables, other crops, ornamental flowering plants, etc. The desired effect can be obtained when the agricultural and horticultural insecticide is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural and horticultural insecticide utilizes so-called penetration and translocation. That is, nursery soil, soil in transplanting holes, plant foot, irrigation water, cultivation water in hydroponics, or the like is treated with the agricultural and horticultural insecticide to allow crops, ornamental flowering plants, etc. to absorb the compound of the present invention through the roots via soil or otherwise.

Examples of useful plants to which the agricultural and horticultural insecticide of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., *chrysanthemum*, rose, carnation, orchid, tulip, lily, etc.), garden trees (e.g., ginkgo trees, cherry trees, Japanese *aucuba*, etc.) and forest trees (e.g., *Abies sachalinensis, Picea jezoensis*, pine, yellow cedar, Japanese cedar, hinoki cypress, *eucalyptus*, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticide of the present invention can be applied to these plants as well.

Further, exemplary toxins expressed in genetically modified plants include insecticidal proteins of *Bacillus cereus* or *Bacillus popilliae; Bacillus thuringiensis* δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticide of the present invention can be used in combination or used systematically.

In order to control target pests, the agricultural and horticultural insecticide of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticide of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of a solid or liquid formulation and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural insecticide of the present invention is commonly used as a formulation convenient for application, which is prepared in the usual method for preparing agrochemical formulations.

That is, the condensed heterocyclic compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticide or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, and also two or more of them may be used in combination.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers may be used alone, and also two or more of them may be used in combination.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, and also two or more of them may be used in combination.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, and also two or more of them may be used in combination.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and Prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural and horticultural insecticide of the present invention can be adjusted as needed, and basically, the amount of the active ingredient compound is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the amount of the active ingredient compound is 0.01 to 50 parts by weight (0.01 to 50% by weight relative to the total weight of the agricultural and horticultural insecticide).

The application rate of the agricultural and horticultural insecticide of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 ares depending on the purpose.

Furthermore, for the expansion of the range of target pests and the appropriate time for pest control, or for dose reduction, the agricultural and horticultural insecticide of the present invention can be used after mixed with other agricultural and horticultural insecticides, acaricides, nematicides, microbicides, biopesticides and/or the like. Further, the agricultural and horticultural insecticide can be used after mixed with herbicides, plant growth regulators, fertilizers and/or the like depending on the situation.

Examples of such additional agricultural and horticultural insecticides, acaricides and nematicides used for the above-mentioned purposes include 3,5-xylyl methylcarbamate (XMC), crystalline protein toxins produced by *Bacillus*

*thuringiensis* such as *Bacillus thuringiensis aizawai, Bacillus thuringiensis israelensis, Bacillus thuringiensis japonensis, Bacillus thuringiensis kurstaki* and *Bacillus thuringiensis tenebrionis*, BPMC, Bt toxin-derived insecticidal compounds, CPCBS (chlorfenson), DCIP (dichlorodiisopropyl ether), D-D (1,3-dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Exemplary agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Exemplary herbicides used for the same purposes as above include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Exemplary biopesticides used for the same purposes as above include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as *Monacrosporium phymatophagum*, *Steinernema carpocapsae*, *Steinernema kushidai* and *Pasteuria penetrans*; microbial pesticides used as a microbicide, such as *Trichoderma lignorum*, *Agrobacterium radiobactor*, *avirulent Erwinia carotovora* and *Bacillus subtilis*; and biopesticides used as a herbicide, such as *Xanthomonas campestris*. Such a combined use of the agricultural and horticultural insecticide of the present invention with the foregoing biopesticide as a mixture can be expected to provide the same effect as above.

Other examples of the biopesticides include natural predators such as *Encarsia formosa*, *Aphidius colemani*, *Aphidoletes aphidimyza*, *Diglyphus isaea*, *Dacnusa sibirica*, *Phytoseiulus persimilis*, *Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

Hereinafter, the production examples of representative compounds of the present invention and their intermediates will be described in more detail, but the present invention is not limited only to these examples.

EXAMPLES

Production Example 1-1

Production Method of N'-Hydroxy-6-(3-methyl-6-pentafluoroethyl-3H-imidazo[4,5-C]pyridazin-2-yl)-5-(ethylsulfonyl)pyridine-3-carboxamidine

[Chem. 12]

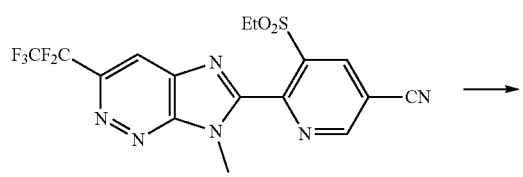

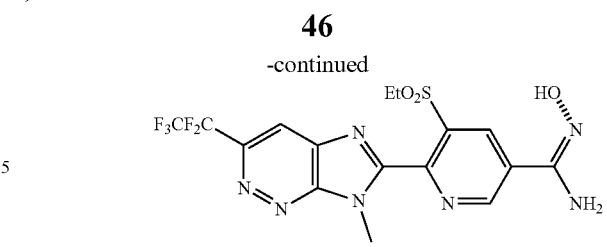

2-(3-Ethylsulfonyl-5-cyanopyridin-2-yl)-3-methyl-6-pentafluoroethyl-3H-imidazo[4,5-C]pyridazine (0.13 g, 0.30 mmol) was dissolved in ethanol (5 mL). To the solution, hydroxyamine hydrochloride (31 mg, 0.45 mmol) and triethylamine (76 mg, 0.75 mmol) were added. The reaction mixture was heated under reflux for 1 hour. The reaction mixture was allowed to cool, and water was added to quench the reaction. Ethyl acetate extraction was performed, followed by washing with brine and drying over anhydrous sodium sulfate. The extract was concentrated to give a crude product. The crude product was purified by silica gel column chromatography to give the title compound (71 mg).

Yield: 49%

Production Example 1-2

Production Method of 3-{2-(3-Methyl-6-pentafluoroethyl-3H-imidazo[4,5-C]pyridazin-2-yl)-3-(ethylsulfonyl)pyridin-5-yl}-5-trifluoromethyl-1,2,4-oxadiazole (compound number 1-41)

[Chem. 13]

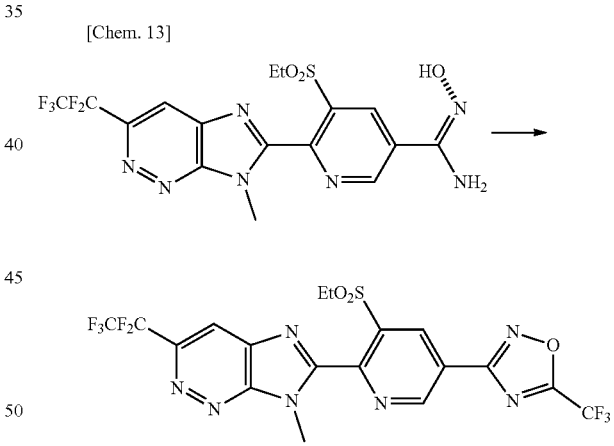

N'-Hydroxy-6-(3-methyl-6-pentafluoroethyl-3H-imidazo [4,5-C]pyridazin-2-yl)-5-(ethylsulfonyl)pyridine-3-carboxamidine (53 mg, 0.11 mmol) was dissolved in toluene (3 mL). To the solution, trifluoroacetic anhydride (0.11 g, 0.55 mmol) was added. The reaction mixture was stirred at 80° C. for 1 hour. The reaction mixture was allowed to cool, and the solvent was evaporated off in vacuo. Ethyl acetate extraction was performed, followed by washing with brine and drying over anhydrous sodium sulfate. The extract was concentrated. The resulting crude product was purified by silica gel column chromatography to give the title compound (54 mg).

Yield: 88%

Physical property: Melting point 177 to 178° C.

Production Example 2

Production Method of 5-{2-(3-Methyl-6-pentafluoroethyl-3H-imidazo[4,5-C]pyridazin-2-yl)-3-(ethylsulfonyl)pyridin-5-yl}-3-phenyl-1,2,4-oxadiazole (compound number 2-56

[Chem. 14]

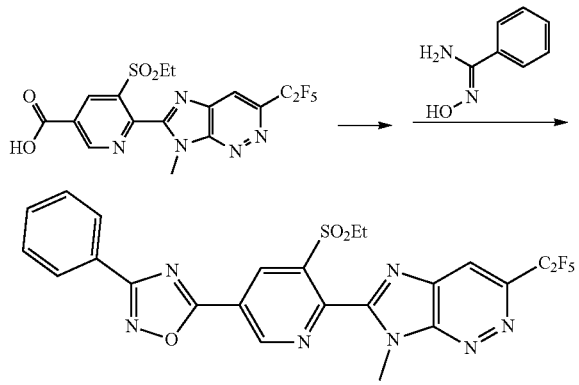

To a THF (2 mL) solution of 2-(3-ethylsulfonyl-5-hydroxycarbonylpyridin-2-yl)-3-methyl-6-pentafluoroethyl-3H-imidazo[4,5-C]pyridazine (0.14 g), oxalyl chloride (0.06 g) and a catalytic amount of DMF (N,N-dimethylformamide) were added, and the mixture was stirred at room temperature for 1 hour. The solvent was concentrated in vacuo, and the residue was dissolved in THF (3 mL). To the solution, triethylamine (0.08 g) and benzamidoxime (0.05 g) were added, and the mixture was stirred at room temperature for 1 hour. The solvent was concentrated in vacuo, and the residue was dissolved in acetic acid (1 mL) and toluene (2 mL). The solution was heated under reflux for 1 hour. The reaction mixture was allowed to cool down to room temperature, and the solvent was concentrated in vacuo. The residue was purified by silica gel column chromatography to give the title compound.

Physical property: Melting point 171 to 172° C.

Reference Example 1

Production of 2-(3-Ethylthio-5-iodopyridin-2-yl)-3-methyl-6-pentafluoroethyl-3H-imidazo[4,5-C]pyridazine

[Chem.15]

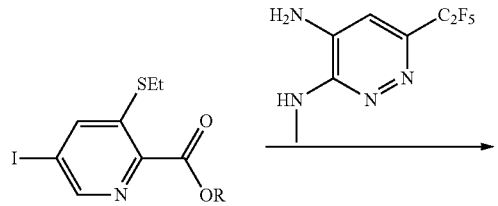

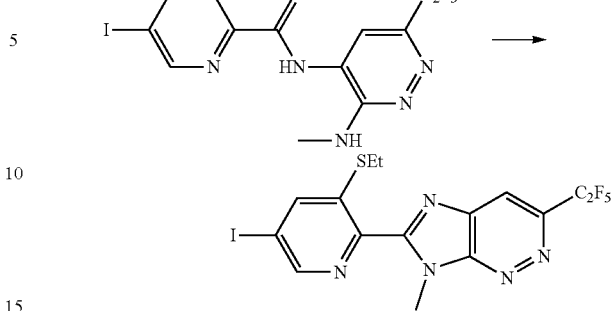

To a THF solution (240 mL) of 4-amino-3-methylamino-6-pentafluoroethyl pyridazine (17.9 g), sodium hydride (3.1 g) was added under ice cooling, and the mixture was stirred until no more bubbles formed. Next, a THF solution (120 mL) of ethyl 3-ethylthio-5-iodo-2-pyridine carboxylate (25 g) was added under ice cooling, and the mixture was allowed to come to room temperature and then stirred for 2 hours. A 0.5 N aqueous hydrochloric acid solution was added to adjust the pH to 3, and ethyl acetate extraction was performed. The organic layer was dried over anhydrous magnesium sulfate and then concentrated in vacuo to give a crude product containing 3-ethylthio-5-iodo-N-(3-methylamino-6-pentafluoroethyl pyridazin-4-yl)-2-pyridine carboxylic acid amide.

Acetic acid (40 mL) was added to a toluene solution (300 mL) of the crude product obtained above, and the mixture was heated under reflux for 6 hours. The reaction mixture was allowed to come to room temperature and then concentrated in vacuo. A saturated aqueous sodium bicarbonate solution was added to the residue, and ethyl acetate extraction was performed. The organic layer was dried over anhydrous magnesium sulfate and then concentrated in vacuo. Small amounts of methyl t-butyl ether and hexane were added to the residue, and the resulting solid was collected by filtration. Thus, the title compound (27 g) was obtained.

Yield: 71%

Physical property: Melting point 127 to 128° C.

Reference Example 2

Production of 2-(3-Ethylsulfonyl-5-iodopyridin-2-yl)-3-methyl-6-pentafluoroethyl-3H-imidazo[4,5-C]pyridazine

[Chem. 16]

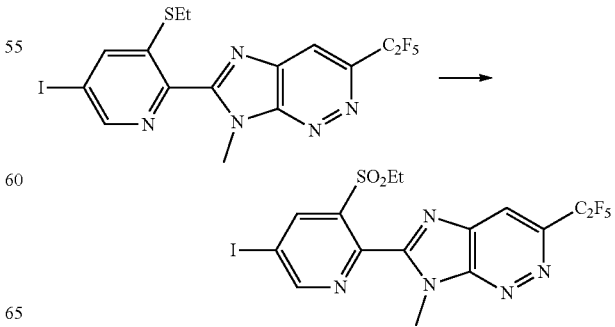

The 2-(3-ethylthio-5-iodopyridin-2-yl)-3-methyl-6-pentafluoroethyl-3H-imidazo[4,5-C]pyridazine (395 mg, 0.766 mmol) obtained in Reference Example 1 was dissolved in ethyl acetate (10 mL). To the solution, m-chloroperoxybenzoic acid (450 mg, 2.2 Eq) was added, and the mixture was stirred at room temperature for 2 hours. To the reaction mixture, several drops of FAMSO (formaldehyde dimethyl dithioacetal S-oxide) and triethylamine (1 mL) were added. The mixture was concentrated and then purified by silica gel column chromatography to give the title compound (406 mg).

Yield: 97%

Reference Example 3

Production Method of 2-(3-Ethylsulfonyl-5-cyanopyridin-2-yl)-3-methyl-6-pentafluoroethyl-3H-imidazo[4,5-C]pyridazine

[Chem. 17]

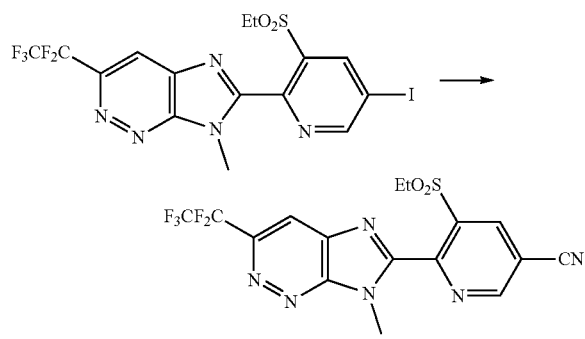

To a pyridine solution (10 mL) of 2-(3-ethylsulfonyl-5-iodopyridin-2-yl)-3-methyl-6-pentafluoroethyl-3H-imidazo[4,5-C]pyridazine (0.50 g, 0.91 mmol), CuCN (0.16 g, 1.8 mmol) was added, and the mixture was stirred at 150° C. for 2 hours. After the completion of the reaction, silica gel was added, and the mixture was concentrated in vacuo. The residue was purified by silica gel column chromatography to give the title compound (0.32 g, 0.72 mmol).

Yield: 78%

Reference Example 4

Production Method of 3-Ethylthio-5-trifluoromethyl-N-(3-methylamino-6-pentafluoroethyl pyridazin-4-yl)-2-pyridine carboxylic acid amide

[Chem. 18]

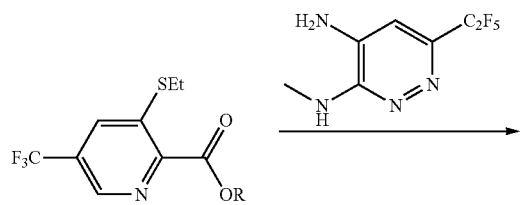

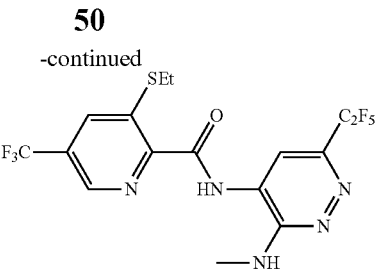

To a tetrahydrofuran solution (240 mL) of 4-amino-3-methylamino-6-pentafluoroethyl pyridazine (17.9 g), sodium hydride (3.1 g) was added under ice cooling, and the mixture was stirred until no more bubbles formed. Next, a tetrahydrofuran solution (120 mL) of ethyl 3-ethylthio-5-trifluoromethyl-2-pyridine carboxylate (25 g) was added under ice cooling, and the mixture was allowed to come to room temperature and then stirred for 2 hours. A 0.5 M aqueous hydrochloric acid solution was added to adjust the pH to 3, and ethyl acetate extraction was performed. The organic layer was dried over anhydrous magnesium sulfate and then concentrated in vacuo to give the title compound (30 g).

Reference Example 5

Production Method of 3-Ethylthio-5-trimethoxymethyl-N-(3-methylamino-6-pentafluoroethyl pyridazin-4-yl)-2-pyridine carboxylic acid amide

[Chem. 19]

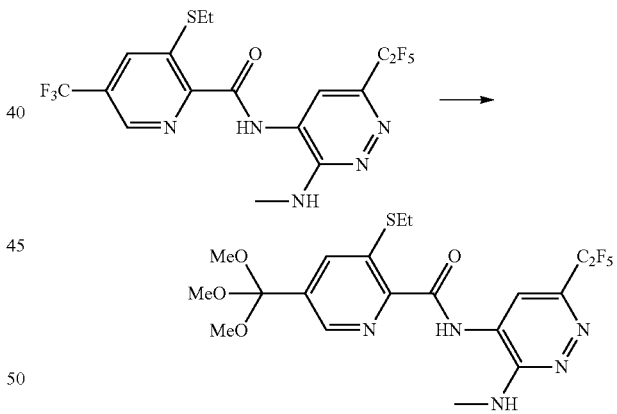

To a methanol (15 mL) solution of the 3-ethylthio-5-trifluoromethyl-N-(3-methylamino-6-pentafluoroethyl pyridazin-4-yl)-2-pyridine carboxylic acid amide (6.9 g) obtained in Reference Example 4, a 28% sodium methoxide solution (28 g) was added, and the mixture was stirred at 50° C. for 4 hours. After that, the reaction mixture was concentrated, diluted hydrochloric acid was added, and ethyl acetate extraction was performed. The organic layer was dried over anhydrous sodium sulfate and then concentrated in vacuo. The residue was purified by silica gel column chromatography to give the title compound (7.4 g).

Physical property: $^1$H-NMR (CDCl$_3$) δ 10.15 (s, 1H), 8.51 (d, 1H), 8.32 (s, 1H), 7.93 (d, 1H), 4.93 (brs, 1H), 3.27 (d, 3H), 3.18 (s, 9H), 3.02 (q, 2H), 1.45 (s, 3H)

Reference Example 6

Production Method of 2-(3-Ethylthio-5-methoxycarbonylpyridin-2-yl)-3-methyl-6-pentafluoroethyl-3H-imidazo[4,5-C]pyridazine

[Chem. 20]

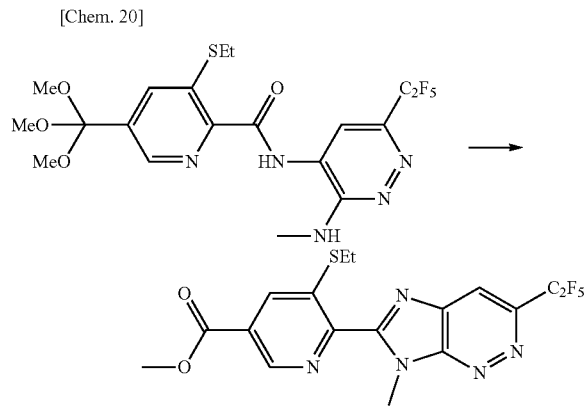

3-Ethylthio-5-trimethoxymethyl-N-(3-methylamino-6-pentafluoroethyl pyridazin-4-yl)-2-pyridine carboxylic acid amide (7.4 g) was added to a mixed solvent of acetic acid (50 mL) and toluene (50 mL), and the mixture was heated under reflux for 1 hour. The reaction mixture was allowed to cool down to room temperature, and the solvent was concentrated in vacuo. The residue was purified by silica gel column chromatography to give the title compound (5.7 g).

Physical property: $^1$H-NMR (CDCl$_3$) δ 9.10 (d, 1H), 8.39 (d, 1H), 8.30 (s, 1H), 4.30 (s, 3H), 4.04 (s, 3H), 3.07 (q, 2H), 1.40 (t, 3H)

Reference Example 7

Production Method of 2-(3-Ethylsulfonyl-5-methoxycarbonylpyridin-2-yl)-3-methyl-6-pentafluoroethyl-3H-imidazo[4,5-C]pyridazine

[Chem. 21]

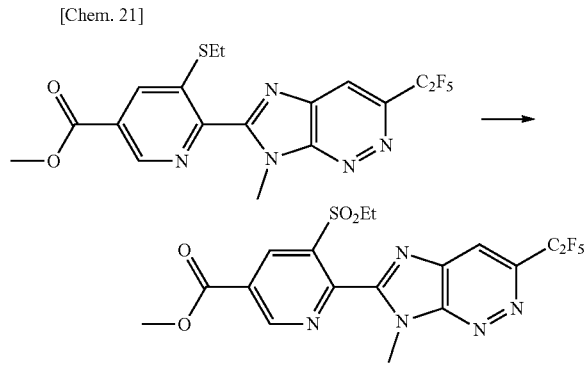

2-(3-Ethylthio-5-methoxycarbonylpyridin-2-yl)-3-methyl-6-pentafluoroethyl-3H-imidazo[4,5-C]pyridazine (5.7 g) was dissolved in ethyl acetate (50 mL). To the solution, 60% m-chloroperoxybenzoic acid (7.3 g) was added, and the mixture was stirred at room temperature for 2 hours. An aqueous sodium thiosulfate solution and a saturated aqueous sodium carbonate solution were added, and ethyl acetate extraction was performed. The organic layer was dried over anhydrous sodium sulfate and then concentrated in vacuo. The residue was purified by silica gel column chromatography to give the title compound (6.0 g).

Physical property: Melting point 205 to 206° C.

Reference Example 8

Production Method of 2-(3-Ethylsulfonyl-5-hydroxycarbonylpyridin-2-yl)-3-methyl-6-pentafluoroethyl-3H-imidazo[4,5-C]pyridazine

[Chem. 22]

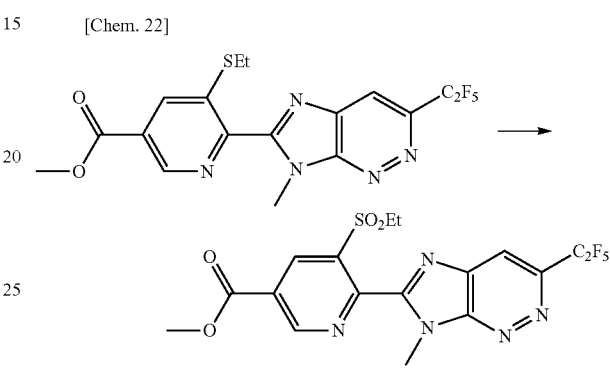

To an ethanol (50 mL) solution of 2-(3-ethylsulfonyl-5-methoxycarbonylpyridin-2-yl)-3-methyl-6-pentafluoroethyl-3H-imidazo[4,5-C]pyridazine (5.0 g), a 15% aqueous sodium hydroxide solution (3.1 g) was added, and the mixture was stirred at room temperature for 2 hours. The solvent was concentrated in vacuo, and the solid residue was dissolved in water. 1 M hydrochloric acid was added under ice cooling to adjust the pH to 3 to 4. The resulting solid was collected by filtration and then dissolved in ethyl acetate. The solution was dried over anhydrous sodium sulfate and then concentrated in vacuo to give the title compound (4.0 g).

Physical property: Melting point 219 to 220° C.

Reference Example 9

Production Method of 5-Chloro-6-ethoxycarbonyl nicotinic acid

[Chem. 23]

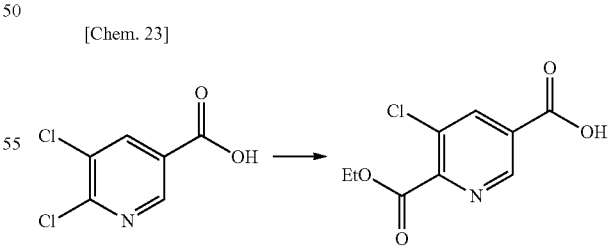

An autoclave was charged with an ethanol (60 mL) solution of 5,6-dichloronicotinic acid (10 g, 52 mmol). To this, DPPB (2.2 g, 10 mol %), triethylamine (14 g, 2.5 Eq) and PdCl$_2$(PPh$_3$)$_2$ (911 mg, 2.5 mol %) were added. The atmosphere in the reaction system was replaced with carbon monoxide (CO pressure, 4.0 MPa), and the mixture was stirred at 135° C. for 4 hours. To the reaction mixture, water and 3 N hydrochloric acid were added to acidify the aqueous layer, and ethyl acetate extraction was performed several times. The organic layer was dried over sodium sulfate and then concentrated, and the solid residue was washed with a hexane-ethyl acetate (2:1) mixture to give the title compound (10.9 g).

Yield: 76%

Physical property: $^1$H-NMR (CDCl$_3$) δ 9.02 (d, 1H), 8.44 (d, 1H), 4.42 (dd, 2H), 1.33 (t, 3H)

Reference Example 10

Production Method of 5-Chloro-6-ethoxycarbonyl nicotinic acid t-butyl ester

[Chem. 24]

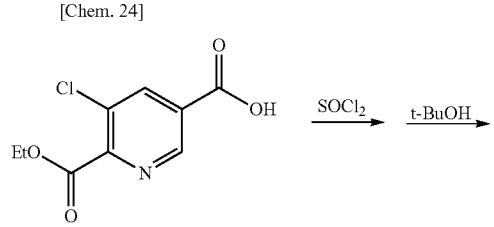

The 5-chloro-6-ethoxycarbonyl nicotinic acid (10.9 g, 47.6 mmol) obtained in Reference Example 9 was dissolved in toluene (30 mL), and DMF (4 mL) was added to the solution. Next, thionyl chloride (11 g, 2 Eq) was added, and the mixture was heated at 90° C. with stirring for 3 hours. The reaction mixture was allowed to come to room temperature and then concentrated. In another vessel, a mixture of t-butanol (35 mL, 10 Eq), THF (100 mL), diisopropylethylamine (50 mL, 7 Eq) and DMAP (4-dimethylaminopyridine) (6 g, 1 Eq) was prepared, and to this, the concentrated residue was slowly added under ice cooling. The reaction mixture was heated under reflux for 3 hours and then allowed to cool down to room temperature. To this, water and ethyl acetate were added, and extraction was performed several times. The organic layer was dried over sodium sulfate and then concentrated. The resulting crude product was purified by silica gel column chromatography to give the title compound (8.43 g).

Yield: 62%

Physical property: $^1$H-NMR (CDCl$_3$) δ 9.05 (d, 1H), 8.30 (d, 1H), 4.50 (dd, 2H), 1.61 (s, 9H), 1.44 (t, 3H)

Reference Example 11

Production Method of 5-Ethylthio-6-ethoxycarbonyl nicotinic acid t-butyl ester

[Chem. 25]

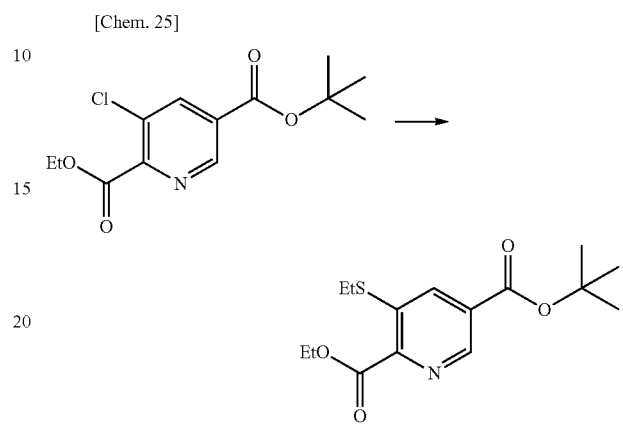

5-Chloro-6-ethoxycarbonyl nicotinic acid t-butyl ester (8.43 g, 21.65 mmol) was dissolved in DMF (100 mL). To the solution, sodium ethanethiolate (2.27 g, 1 Eq) was slowly added under ice cooling, and the mixture was stirred for 5 minutes. To this, water and 0.5 N hydrochloric acid were successively added. After ethyl acetate extraction was performed several times, the organic layer was dried over sodium sulfate and then concentrated. The resulting crude product was purified by column chromatography to give the title compound (6.17 g).

Yield: 92%

Physical property: $^1$H-NMR (CDCl$_3$) δ 8.91 (d, 1H), 8.22 (d, 1H), 4.49 (dd, 2H), 2.99 (dd, 2H), 1.61 (s, 9H), 1.45 (t, 3H), 1.40 (t, 3H)

Reference Example 12

Production Method of 3-Ethylthio-5-t-butoxycarbonylamino picolinic acid ethyl ester

[Chem. 26]

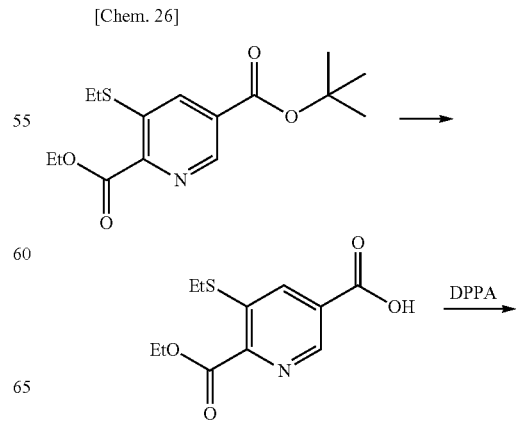

-continued

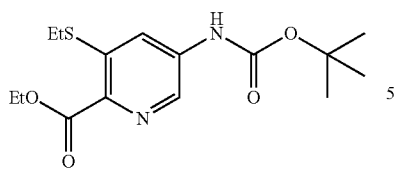

5-Ethylthio-6-ethoxycarbonyl nicotinic acid t-butyl ester (6.17 g, 19.9 mmol) was dissolved in trifluoroacetic acid (30 mL), and the solution was heated under reflux for 30 minutes. The reaction mixture was concentrated, toluene and ethyl acetate were added to the residue, and the mixture was concentrated again. To the residue, t-butanol (100 mL), triethylamine (6.5 g, 3 Eq) and diphenylphosphoryl azide (DPPA) (11.74 g, 2 Eq) were added, and the mixture was stirred at room temperature for 1 hour and then refluxed for 4 hours. The reaction mixture was concentrated and then purified by silica gel column chromatography to give the title compound (3.63 g).

Yield: 56%

Physical property: $^1$H-NMR (CDCl$_3$) δ 8.25 (d, 1H), 8.09 (d, 1H), 6.74 (s, 1H), 4.46 (dd, 2H), 2.97 (dd, 2H), 1.53 (s, 9H), 1.44 (t, 3H), 1.41 (t, 3H)

Reference Example 13

Production Method of 5-Amino-3-ethylthiopicolinic acid ethyl ester

[Chem. 27]

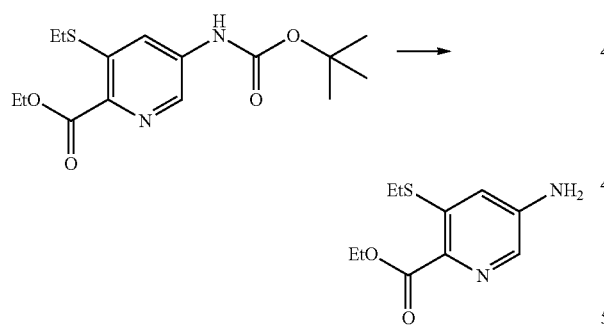

3-Ethylthio-5-t-butoxycarbonylamino picolinic acid ethyl ester (670 mg, 2.06 mmol) was dissolved in trifluoroacetic acid (30 mL), and the solution was stirred at room temperature for 30 minutes. The reaction mixture was concentrated, and water, ethyl acetate and potassium carbonate were added to the residue. After ethyl acetate extraction was performed several times, the organic layer was dried over sodium sulfate and then concentrated. The resulting crude product was purified by silica gel column chromatography to give the title compound (358 mg).

Yield: 77%

Physical property: $^1$H-NMR (CDCl$_3$) δ 7.89 (d, 1H), 6.80 (s, 1H), 4.43 (dd, 2H), 4.08 (s, 2H), 2.88 (dd, 2H), 1.56 (s, 9H), 1.42 (t, 3H), 1.40 (t, 3H)

Reference Example 14

Production Method of 3-Ethylthio-5-iodopicolinic acid ethyl ester

[Chem. 28]

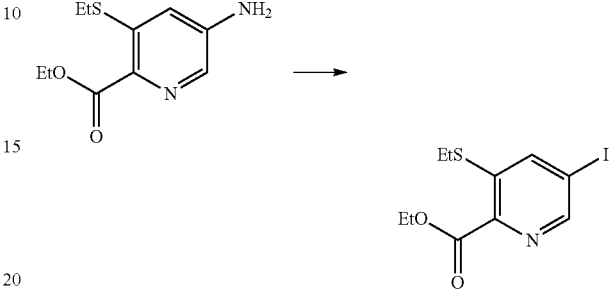

5-Amino-3-ethylthiopicolinic acid ethyl ester (1 g, 4.44 mmol) was dissolved in acetonitrile (10 mL). To the solution, trifluoroacetic acid (500 mg, 1 Eq) and p-toluenesulfonic acid (2.6 g, 3 Eq) were added, and the mixture was cooled in a water bath at about 5° C. To the reaction mixture, an aqueous solution (10 mL) of potassium iodide (2.25 g, 3 Eq) and sodium nitrite (612 mg, 2 Eq) prepared in another vessel was slowly added. The mixture was stirred for 30 minutes and further stirred at room temperature for 30 minutes. To the reaction mixture, an aqueous "hypo" (sodium hyposulfite) solution was added. After ethyl acetate extraction was performed several times, the organic layer was dried and then concentrated. The resulting crude product was subjected to silica gel column chromatography to give the title compound.

Yield: 51%

Physical property: $^1$H-NMR (CDCl$_3$) δ 8.61 (s, 1H), 7.95 (s, 1H), 4.45 (dd, 2H), 2.91 (dd, 2H), 1.43 (t, 3H), 1.39 (t, 3H)

Reference Example 15

Production Method of 3-Ethylthio-5-iodopicolinic acid

[Chem. 29]

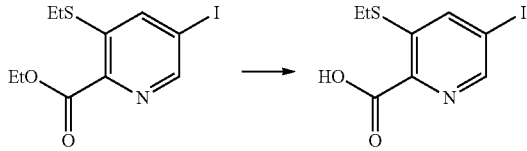

3-Ethylthio-5-iodo-2-pyridine carboxylic acid ethyl ester (761 mg, 2.26 mmol) was dissolved in ethanol (5 mL), and a 3 N aqueous sodium hydroxide solution (1.2 mL, 1.5 Eq) was added. The mixture was stirred at room temperature for 5 minutes, and water and 3 N hydrochloric acid were added. After ethyl acetate extraction was performed several times, the organic layer was dried and then concentrated to give the title compound in a quantitative yield.

Yield: quantitative
Physical property: $^1$H-NMR (CDCl$_3$) δ 13.30 (brs, 1H), 8.60 (d, 1H), 8.16 (d, 1H), 3.00 (dd, 2H), 1.24 (t, 3H)

Reference Example 16

Production Method of 3-Chloro-5-trifluoromethylpyridine carboxylic acid methyl ester

[Chem. 30]

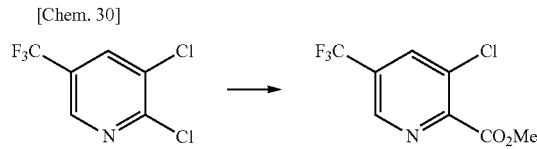

A 200-mL autoclave was charged with 2,3-dichloro-5-trifluoromethylpyridine (30 g, 0.14 mol), triethylamine (21 mL, 0.15 mol, 1.1 Eq), PdCl$_2$ (tpp)$_2$ (0.97 g, 1.4 mmol, 1 mol %), DPPB (1,4-bis(diphenylphosphino)butane) (0.59 g, 1.38 mmol, 1 mol %) and methanol (70 mL). The atmosphere in the reaction system was replaced with carbon monoxide at 3 MPa 3 times. The reaction was started at an initial pressure of 3.0 MPa at a temperature of 85° C. and at an agitation speed of 600 rpm. During the reaction, carbon monoxide was added as appropriate so that the internal pressure may not fall below 3.0 MPa, and the temperature was raised by 10° C. per hour until it reached 115° C. After carbon monoxide absorption stopped, the reaction mixture was allowed to cool down to room temperature. This was suspended in ethyl acetate, the suspension was filtered in vacuo, and the filtrate was concentrated in vacuo. The residue was redissolved in ethyl acetate, and the solution was washed with 1 N hydrochloric acid and brine, and then dried over anhydrous sodium sulfate. The organic layer was concentrated to give the title compound (35.4 g).

Physical property: $^1$H-NMR (CDCl$_3$) δ 8.65 (d, 1H), 7.86 (d, 1H), 4.04 (s, 3H), 2.99 (q, 2H), 1.43 (t, 3H)

Reference Example 17

Production Method of 3-Ethylthio-5-trifluoromethylpyridine carboxylic acid methyl ester

[Chem. 31]

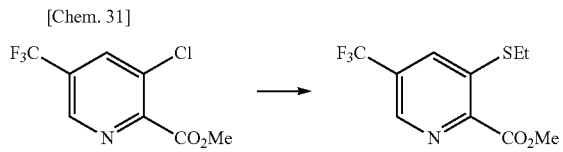

The 3-chloro-5-trifluoromethylpyridine carboxylic acid methyl ester (1 g, 4.1 mmol) synthesized in Reference Example 16 was dissolved in DMF (4.1 mL). To the solution, 80% sodium ethanethiolate (460 mg, 4.4 mmol, 1.1 Eq) was added under ice cooling, and the mixture was stirred for 30 minutes. The reaction mixture was diluted with ethyl acetate, washed successively with a saturated aqueous sodium bicarbonate solution, brine, water and brine, and dried over anhydrous sodium sulfate. The resulting crude product was purified by silica gel column chromatography to give the title compound (818 mg, 3.1 mmol).

Yield: 74%

Reference Example 18

Synthesis of 3-Methylamino-6-pentafluoroethyl pyridazine

[Chem. 32]

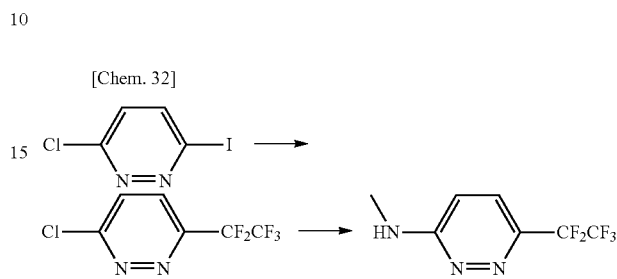

Under an argon atmosphere, 3-chloro-6-iodopyridazine (7.2 g) synthesized according to the method described in the previously-mentioned reference, copper iodide (2.86 g), 1,10-phenanthroline (2.7 g) and a solution (ca. 0.33 M, 80 mL) of a bisfluoro alkyl zinc reagent in N-methylpyrrolidone (NMP) prepared according to the method described in Program and Abstracts of the 94th Spring Annual Meeting (presentation No. 2B1-17, p. 1229) were mixed in a vessel with stirring at 90° C. for 40 minutes, and then allowed to cool down to room temperature. In another vessel, a mixture of THF (30 mL) and methylamine (30 mL of a 10 M solution of methylamine in methanol) was prepared, and to this, the reaction mixture was slowly added dropwise under ice cooling. The mixture was heated to room temperature and stirred for 1 hour. After addition of water and ethyl acetate, the mixture was stirred for 5 minutes and then filtered through Celite. The filtrate was extracted with ethyl acetate 3 times. The organic layer was dried over sodium sulfate and then concentrated. The resulting crude product was purified by silica gel column chromatography to give the title compound (6.36 g).

Physical property: Melting point 141 to 143° C.

Reference Example 19

Synthesis of 4-Bromo-3-methylamino-6-pentafluoroethyl pyridazine

[Chem. 33]

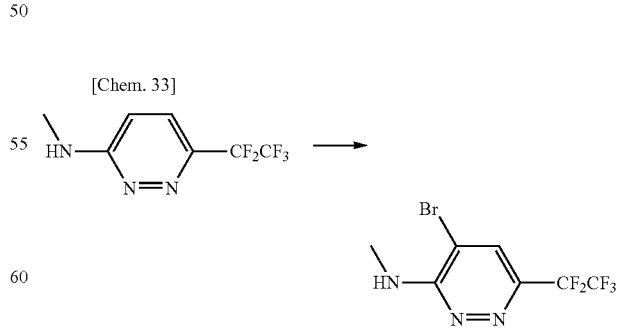

3-Methylamino-6-pentafluoroethyl pyridazine (6.05 g) was dissolved in acetic acid (50 mL). To the solution, 1,3-dibromo-5,5-dimethylhydantoin (8.4 g) was added, and the mixture was heated at 95° C. with stirring for 3 hours.

The reaction mixture was concentrated, and water was added to the residue. This was neutralized with potassium carbonate, and ethyl acetate extraction was performed 3 times. The organic layer was dried over sodium sulfate and then concentrated. The resulting crude product was purified by silica gel column chromatography to give the title compound (6.16 g).

Yield: 76%

Physical property: Melting point 41 to 43° C.

Reference Example 20

Synthesis of 4-Amino-3-methylamino-6-pentafluoroethyl pyridazine

[Chem. 34]

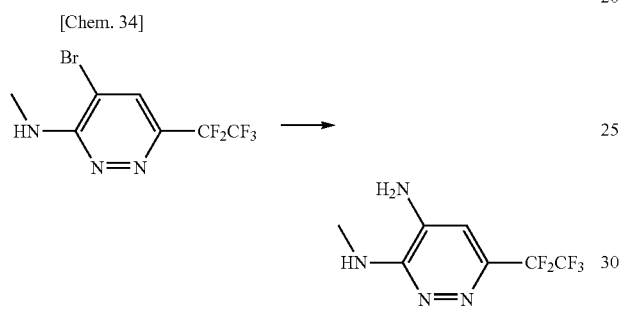

An autoclave was charged successively with 4-bromo-3-methylamino-6-pentafluoroethyl pyridazine (6.16 g), copper (I) oxide (1.44 g), NMP (30 mL) and a 28% aqueous ammonia solution (30 mL), purged with argon, and then sealed. The mixture in the autoclave was heated at 80° C. with stirring for 3 hours and then allowed to cool down to room temperature. After addition of water and ethyl acetate, the mixture was stirred for 5 minutes and then filtered through Celite. The filtrate was extracted with ethyl acetate 3 times. The organic layer was dried over sodium sulfate and then concentrated. The resulting crude product was purified by silica gel column chromatography to give the title compound (3.39 g).

Yield: 69%

Physical property: $^1$H-NMR (CDCl$_3$) δ 6.75 (s, 1H), 5.18 (s, 1H), 4.59 (s, 2H), 2.85 (s, 3H)

Hereinafter, formulation examples are shown, but the present invention is not limited thereto. In the formulation examples, the "parts" means parts by weight.

Formulation Example 1

| Compound of the present invention | 10 parts |
| --- | --- |
| Xylene | 70 parts |
| N-methylpyrrolidone | 10 parts |
| Equal-weight mixture of polyoxyethylene nonylphenyl ether and calcium alkylbenzene sulfonate | 10 parts |

The above ingredients are uniformly mixed for dissolution to give an emulsifiable concentrate formulation.

Formulation Example 2

| Compound of the present invention | 3 parts |
| --- | --- |
| Clay powder | 82 parts |
| Diatomite powder | 15 parts |

The above ingredients are uniformly mixed and then pulverized to give a dust formulation.

Formulation Example 3

| Compound of the present invention | 5 parts |
| --- | --- |
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granular formulation.

Formulation Example 4

| Compound of the present invention | 20 parts |
| --- | --- |
| Kaolin and synthetic high-dispersion silicic acid | 75 parts |
| Equal-weight mixture of polyoxyethylene nonylphenyl ether and calcium alkylbenzene sulfonate | 5 parts |

The above ingredients are uniformly mixed and then pulverized to give a wettable powder formulation.

Hereinafter, test examples in connection with the present invention are shown, but the present invention is not limited thereto.

Test Example 1

Test for Control Effect on *Myzus persicae*

Chinese cabbage plants were planted in plastic pots (diameter: 8 cm, height: 8 cm), green peach aphids (*Myzus persicae*) were propagated on the plants, and the number of surviving green peach aphids in each pot was counted. The heterocycle-bound condensed heterocyclic compounds represented by the general formula (1) of the present invention or salts thereof were separately dispersed in water and diluted to 500 ppm. The agrochemical dispersions were applied to the foliage of the potted Chinese cabbage plants. After the plants were air-dried, the pots were kept in a greenhouse. At 6 days after the foliar application, the number of surviving green peach aphids on the Chinese cabbage plant in each pot was counted, the control rate was calculated according to the formula shown below, and the control effect was evaluated according to the criteria shown below.

Control rate=100−{(T×Ca)/(Ta×C)}×100  [Math. 1]

Ta: the number of survivors before the foliar application in a treatment plot
T: the number of survivors after the foliar application in a treatment plot
Ca: the number of survivors before the foliar application in a non-treatment plot C: the number of survivors after the foliar application in a non-treatment plot
Criteria
A: the control rate is 100%.
B: the control rate is 90 to 99%.
C: the control rate is 80 to 89%.
D: the control rate is 50 to 79%.

As a result, the compounds 1-2, 1-6, 1-29, 1-30, 1-34, 1-41, 1-42, 1-56, 1-62 and 2-56 of the present invention showed the activity level evaluated as A.

Test Example 2

Insecticidal test on *Laodelphax striatella*

The heterocycle-bound condensed heterocyclic compounds represented by the general formula (1) of the present invention or salts thereof were separately dispersed in water and diluted to 500 ppm. Rice plant seedlings (variety: Nihonbare) were dipped in the agrochemical dispersions for 30 seconds. After air-dried, each seedling was put into a separate glass test tube and inoculated with ten 3rd-instar larvae of *Laodelphax striatella*, and then the glass test tubes were capped with cotton plugs. At 8 days after the inoculation, the numbers of surviving larvae and dead larvae were counted, the corrected mortality rate was calculated according to the formula shown below, and the insecticidal effect was evaluated according to the criteria shown below.

Corrected mortality rate (%)=100×(Survival rate in a non-treatment plot−Survival rate in a treatment plot)/Survival rate in a non-treatment plot  [Math. 2]

Criteria
A: the corrected mortality rate is 100%.
B: the corrected mortality rate is 90 to 99%.
C: the corrected mortality rate is 80 to 89%.
D: the corrected mortality rate is 50 to 79%.

As a result, the compounds 1-2, 1-6, 1-29, 1-30, 1-34, 1-41, 1-42, 1-56, 1-62 and 2-56 of the present invention showed the activity level evaluated as A.

Test Example 3

Insecticidal Test on *Plutella xylostella*

Adults of *Plutella xylostella* were released onto Chinese cabbage seedlings and allowed to lay eggs thereon. At 2 days after the release of the adults, the Chinese cabbage seedlings with laid eggs were dipped for about 30 seconds in agrochemical dispersions diluted to 500 ppm, each of which contained a different kind of heterocycle-bound condensed heterocyclic compound represented by the general formula (1) of the present invention as an active ingredient. After air-dried, the seedlings were kept in a thermostatic chamber at 25° C. At 6 days after the dip treatment, the number of hatched larvae per plot was counted, the mortality rate was calculated according to the formula shown below, and the insecticidal effect was evaluated according to the criteria of Test Example 2. This test was conducted in triplicate using 10 adults of *Plutella xylostella* per plot.

Corrected mortality rate (%)=100×(Number of hatched larvae in a non-treatment plot−Number of hatched larvae in a treatment plot)/Number of hatched larvae in a non-treatment plot  [Math. 3]

As a result, the compounds 1-2, 1-6, 1-29, 1-30, 1-34, 1-41, 1-42, 1-56, 1-62 and 2-56 of the present invention showed the activity level evaluated as A.

INDUSTRIAL APPLICABILITY

The compound of the present invention is highly effective for the control of a wide range of agricultural and horticultural pests and thus is useful.

The invention claimed is:

1. A heterocycle-bound condensed heterocyclic compound represented by the formula (1a-1)':

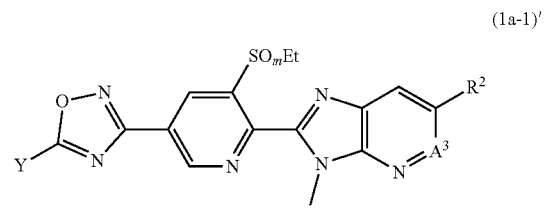

(1a-1)'

{wherein
R$^2$ represents:
(b4) a halo (C$_1$-C$_6$) alkyl group;
Y represents:
(c5) a (C$_1$-C$_6$) alkyl group; or
(c6) a (C$_3$-C$_6$) cycloalkyl group;
A$^3$ is CH or a nitrogen atom, and
m represents 2}
or a salt thereof.

2. The heterocycle-bound condensed heterocyclic compound or the salt thereof according to claim 1, wherein
R$^2$ is: CF$_3$ or C$_2$F$_5$, and
Y is: methyl, a cyclopropyl group, or a cyclobutyl group.

3. The heterocycle-bound condensed heterocyclic compound or the salt thereof according to claim 2, wherein A$^3$ is CH.

4. The heterocycle-bound condensed heterocyclic compound or the salt thereof according to claim 2, wherein A$^3$ is a nitrogen atom.

5. An agricultural or horticultural insecticide comprising the heterocycle-bound condensed heterocyclic compound or the salt thereof according to claim 1 as an active ingredient.

6. A method of using the agricultural or horticultural insecticide according to claim 5, the method comprising applying an insecticidally effective amount of the heterocycle-bound condensed heterocyclic compound or the salt thereof according to claim 1 to plants or soil.

7. An animal ectoparasite control agent comprising the heterocycle-bound condensed heterocyclic compound or the salt thereof according to claim 1 as an active ingredient.

* * * * *